US011718572B2

(12) United States Patent
Luo et al.

(10) Patent No.: US 11,718,572 B2
(45) Date of Patent: Aug. 8, 2023

(54) METHODS FOR OPERATING INTEGRATED CHEMICAL PROCESSING SYSTEMS FOR PRODUCING OLEFINS

(71) Applicant: Dow Global Technologies LLC, Midland, MI (US)

(72) Inventors: Lin Luo, Sugar Land, TX (US); Hangyao Wang, Pearland, TX (US); Yu Liu, Lake Jackson, TX (US); Barry B. Fish, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/621,949

(22) PCT Filed: Jun. 8, 2020

(86) PCT No.: PCT/US2020/036582
§ 371 (c)(1),
(2) Date: Dec. 22, 2021

(87) PCT Pub. No.: WO2020/263544
PCT Pub. Date: Dec. 30, 2020

(65) Prior Publication Data
US 2022/0251006 A1  Aug. 11, 2022

Related U.S. Application Data

(60) Provisional application No. 62/865,597, filed on Jun. 24, 2019.

(51) Int. Cl.
*C07C 7/167* (2006.01)
*B01D 3/14* (2006.01)
(Continued)

(52) U.S. Cl.
CPC ............... *C07C 7/167* (2013.01); *B01D 3/14* (2013.01); *B01J 23/62* (2013.01); *C07C 5/03* (2013.01);
(Continued)

(58) Field of Classification Search
CPC ........... C07C 7/167; C07C 5/03; C07C 7/005; C07C 7/04; C07C 2523/62; C07C 5/3337;
(Continued)

(56) References Cited

U.S. PATENT DOCUMENTS 5,220,097 A   6/1993   Lam et al.
5,753,583 A   5/1998   Heineke et al.
(Continued)

FOREIGN PATENT DOCUMENTS

CN    109689600 A     4/2019
WO    2018/024650 A1  2/2018

OTHER PUBLICATIONS

International Search Report and Written Opinion issued by the European Patent Office acting as International Searching Authority for International Patent Application No. PCT/US2020/036582 dated Sep. 25, 2020 (16 total pages).
(Continued)

*Primary Examiner* — Ali Z Fadhel
(74) *Attorney, Agent, or Firm* — Dinsmore & Shohl LLP

(57) ABSTRACT

A method for operating an integrated system for producing olefins may include contacting a hydrogenation feed with a first hydrogenation catalyst to produce a hydrogenated effluent, the hydrogenation feed including at least a portion of a first process effluent from a first olefin production process and at least a portion of a second process effluent from a second olefin production process. The hydrogenation feed may include at least hydrogen, ethylene, carbon monoxide, acetylene, methyl acetylene, and propadiene, and the first
(Continued)

hydrogenation catalyst may be a hydrogenation catalyst having a temperature operating range of at least 40° C. The hydrogenated effluent may include methyl acetylene, propadiene, or both. The method may further include contacting at least a portion of the hydrogenated effluent with a second hydrogenation catalyst, which may cause hydrogenation of at least a portion of the methyl acetylene and propadiene to produce an MAPD hydrogenated effluent.

15 Claims, 7 Drawing Sheets

(51) Int. Cl.
| | | |
|---|---|---|
| | *B01J 23/62* | (2006.01) |
| | *C07C 5/03* | (2006.01) |
| | *C07C 7/00* | (2006.01) |
| | *C07C 7/04* | (2006.01) |

(52) U.S. Cl.
CPC ............... *C07C 7/005* (2013.01); *C07C 7/04* (2013.01); *C07C 2523/62* (2013.01)

(58) Field of Classification Search
CPC .. C07C 4/04; C07C 4/06; C07C 11/04; C07C 11/06; B01D 3/14; B01J 23/62
See application file for complete search history.

(56) References Cited

U.S. PATENT DOCUMENTS

| | | | |
|---|---|---|---|
| 5,847,250 A | 12/1998 | Flick et al. | |
| 5,925,799 A * | 7/1999 | Stanley | C10G 45/32 |
| | | | 208/143 |
| 8,563,793 B2 | 10/2013 | Zimmermann et al. | |
| 11,584,700 B2 | 2/2023 | Wang et al. | |
| 2004/0176652 A1* | 9/2004 | Molinier | C10G 45/32 |
| | | | 585/265 |
| 2004/0192982 A1* | 9/2004 | Kuechler | C10G 45/40 |
| | | | 585/259 |
| 2006/0025641 A1* | 2/2006 | Gartside | C07C 7/167 |
| | | | 585/260 |
| 2006/0173224 A1* | 8/2006 | Putman | C10G 45/38 |
| | | | 502/263 |
| 2012/0107182 A1 | 5/2012 | Wegerer et al. | |
| 2012/0108865 A1 | 5/2012 | Wegerer et al. | |
| 2014/0249339 A1 | 9/2014 | Simanzhenkov et al. | |
| 2016/0355449 A1* | 12/2016 | Odi | C07C 5/08 |
| 2016/0362616 A1 | 12/2016 | Oprins | |
| 2017/0137346 A1* | 5/2017 | Bergmeister, III | B65G 1/10 |
| 2019/0161422 A1 | 5/2019 | Pretz et al. | |
| 2021/0371357 A1 | 12/2021 | Luo et al. | |
| 2022/0227687 A1 | 7/2022 | Luo et al. | |
| 2022/0251006 A1 | 8/2022 | Luo et al. | |

OTHER PUBLICATIONS

International Search Report/Written Opinion for PCT/US2020/036590 dated Sep. 25, 2020, pp. 1-17.
International Search Report/Written Opinion for PCT/US2020/036586 dated Aug. 28, 2020, pp. 1-17.
Communication Pursuant to Rules 161/162 for Application No. 20735721.1 dated Feb. 3, 2022—pp. 1-3.
Communication Pursuant to Rules 161/162 for Application No. 20750466.3 dated Feb. 3, 2022—pp. 1-3.
Communication Pursuant to Rules 161/162 for Application No. 20750465.5 dated Feb. 11, 2022—pp. 1-3.
International Preliminary Report on Patentability for Application No. PCT/US2020/036590 dated Dec. 28, 2021, pp. 1-11.
International Preliminary Report on Patentability for Application No. PCT/US2020/036586 dated Dec. 28, 2021, pp. 1-11.
International Preliminary Report on Patentability for Application No. PCT/US2020/03682 dated Dec. 28, 2021, pp. 1-10.
Edgar L. Mohundro, "Overview on C2 and C3 Selective Hydrogenation in Ethylene Plants", 15th Ethylene Produces Conference, 2003 AICHE Spring National Meeting, New Orleans, LA.
Notice of Allowance dated Mar. 15, 2023, pertaining to U.S. Appl. No. 17/621,945, 17 pgs.
Chinese Office Action dated Mar. 4, 2023, pertaining to CN Patent Application No. 202080046062.X, 22 pgs.
Hao et al. "Alleviate CO Effect on Front-end Acetylene Converter", Chemical Industry and Engineering Progress, vol. 21, No. 9, 2002, pp. 673-675.

* cited by examiner

METHODS FOR OPERATING INTEGRATED CHEMICAL PROCESSING SYSTEMS FOR PRODUCING OLEFINS

CROSS-REFERENCE TO RELATED APPLICATIONS

This application is a National Stage Entry under 35 U.S.C. § 371 of International Patent Application No. PCT/US2020/036582, filed Jun. 8, 2020, which claims priority to U.S. Provisional Patent Application No. 62/865,597, filed on Jun. 24, 2019, the entire disclosures of both of which are hereby incorporated by reference.

BACKGROUND

Field

The present disclosure generally relates to chemical processing systems for producing olefins and the operation thereof and, more specifically, to methods for operating integrated olefin production processes to remove byproducts of the olefin production processes.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as natural gas condensate or a product stream from a petrochemical operation. For example, hydrocarbon cracking (e.g., steam cracking), catalytic dehydrogenation, methanol-to-olefin processes, dehydration processes, or other processes may be used to produce olefins from a hydrocarbon stream. However, hydrocarbon cracking and other processes for producing light olefins can also produce byproducts and impurities, such as acetylenic and allenic compounds, which can decrease the effectiveness of downstream processes and catalysts. Additionally, the presence of high concentrations of acetylenic and allenic compounds may present a safety concern in downstream processes due to the reactivity of these compounds. Acetylene, methyl acetylene, propadiene, and other impurities and byproducts can be removed from an olefin-containing hydrocarbon cracking effluent or other process effluent through hydrogenation in a selective hydrogenation process downstream of the hydrocarbon cracking unit or other olefin production process. Selective hydrogenation of acetylenic and allenic compounds in the hydrocarbon cracking effluent or other process effluent can also recover additional product olefins, such as ethylene and propylene.

SUMMARY

In some olefin production processes, light olefins, such as ethylene and propylene, for example, may be produced through a combination of one or more olefin production processes, such as steam cracking, fluidized catalytic dehydrogenation (FCDh), methanol-to-oil processes, dehydration processes, or other olefin production processes. Because of similarities in the compositions of effluents from these processes, two or more of these separate olefin production processes can be integrated to make use of a single effluent processing system operable to purify and separate the effluent streams. For example, a steam cracking system and an FCDh system can be integrated so that the cracked gas from steam cracking system and at least a portion of the FCDh effluent from the FCDh system can be combined and processed in a common effluent processing system downstream of the steam cracking system and FCDh system. The effluent processing system may include various separation and purification systems to isolate product and/or recycle streams and remove unwanted contaminants and reaction byproducts. The effluent processing system may include an acetylene hydrogenation unit operable for hydrogenating acetylene produced in the steam cracking unit or other olefin production processes.

The acetylene hydrogenation unit can be sensitive to the concentration of carbon monoxide (CO) in the feedstream to the acetylene hydrogenation unit. Not intending to be limited by any particular theory, it is believed that CO may interact with the hydrogenation catalyst in the acetylene hydrogenation unit to decrease the activity of the hydrogenation catalyst for hydrogenating acetylene. Conversely, decreasing the CO concentration in the acetylene hydrogenation unit may increase the activity of the hydrogenation catalyst. A sudden decrease in the CO concentration in the hydrogenation feed to the acetylene hydrogenation unit may increase the activity of the hydrogenation catalyst, which can lead to increased hydrogenation of olefin products in the hydrogenation feed, such as ethylene and propylene, and reduced olefin selectivity. Hydrogenation of olefins is exothermic. Therefore, rapid increases in hydrogenation of olefins, such as ethylene and propylene, may lead to thermal runaway of the acetylene hydrogenation unit due to rapid heat release from the olefin hydrogenation reactions.

In one or more embodiments, an effluent from a first olefin production process may have a concentration of CO greater than the concentration of CO in an effluent from a second olefin production process integrated with the first olefin production process. For example, an FCDh effluent from an FCDh process may have a greater concentration of CO than a concentration of CO in the cracked gas from a steam cracking unit. Therefore, when an integrated process for producing olefins is operating with both the cracked gas and at least a portion of an FCDh effluent being passed to the effluent processing system, the concentration of CO in the feed to the acetylene hydrogenation unit may be substantially greater (e.g., at least 25% greater, or even 100% greater or more) than the concentration of CO from the cracked gas only. A discontinuity in operation of the FCDh system, such as during an unexpected FCDh trip, may cause a sudden decrease in or complete loss of flow of the FCDh effluent to the effluent processing system. This can lead to a sudden and significant decrease in the CO concentration of the hydrogenation feed. As previously discussed, a sudden reduction in the CO concentration may lead to thermal runaway of the acetylene hydrogenation unit due to the sudden increased hydrogenation of olefin products and the generation of heat from the exothermic hydrogenation reaction. Thus, a sudden decrease in or complete loss of flow of the FCDh effluent or other olefin production process effluent to the effluent processing system may lead to thermal runaway of the acetylene hydrogenation reactor. The sudden decrease or loss of the flow of FCDh effluent to the effluent processing system may also decrease the total flow rate of reactants through the acetylene hydrogenation unit, resulting in smaller Gas Hourly Space Velocity (GHSV) or longer residence time for the hydrogenation feed, which may also increase the conversion of olefins and lead to thermal runaway. The increased temperatures in excess of 200° C. experienced during thermal runaway can trip the acetylene hydrogenation unit, sometimes resulting in restart of the system. Additionally, the increased temperatures in excess of 200° C. can damage the hydrogenation catalyst and equipment, such as reactors, instruments, heat exchangers, and other equipment, and may increase safety risks. In many runaway situations, severe loss of catalyst performance resulting from thermal runaway can require catalyst replacement which leads to significant unit down time. Thermal runaway can also result in increased loss of olefin products through over-hydrogenation of the ethylene and propylene.

The methods disclosed herein may reduce or prevent thermal runaway of the acetylene hydrogenation unit of an integrated process for producing olefins, such as an integrated process that combines a steam cracking system and an FCDh system, in response to a sudden decrease in CO concentration caused by the loss of flow of an effluent from one of the integrated olefin processes. In particular, the methods disclosed herein may reduce or prevent thermal runaway of the acetylene hydrogenation unit by utilizing a first hydrogenation catalyst having a temperature operating range of greater than or equal to 40° C. for a given hydrogenation feed composition. The temperature operating range of the first hydrogenation catalyst may be the difference between a clean-up temperature and a runaway temperature, at which 3 wt. % of the ethylene in the hydrogenation feed is hydrogenated in the acetylene hydrogenation unit. The clean-up temperature may be a temperature at which the concentration of acetylene in the hydrogenated effluent is equal to a target acetylene concentration set by a downstream user or customer, such as 1 part per million by volume or other value set by downstream users or customers. The greater temperature operating range of the first hydrogenation catalyst may cause the first hydrogenation catalyst to be less responsive to sudden changes in the carbon monoxide concentration of the hydrogenation feed and may allow operation of the acetylene hydrogenation unit to vary within the broad temperature operating range without causing thermal runaway of the acetylene hydrogenation unit.

Although effective to reduce or prevent thermal runaway of the acetylene hydrogenation unit, the first hydrogenation catalyst may have decreased activity for hydrogenating methyl acetylene (MA) and propadiene (PD), which may be produced in one or more of the integrated olefin processes, such as in a steam cracking process, and which may be present in the hydrogenation feed. MA and PD can produce coke when streams containing the MA and/or the PD are recycled back to an olefin production process, such as an FCDh system, or passed to downstream processes. Additionally, specifications from olefin users may require reduced concentrations of MA and PD below threshold concentrations for these compounds. The systems and methods disclosed herein may additionally include a methyl acetylene/propadiene hydrogenation unit (MAPD hydrogenation unit) downstream of the acetylene hydrogenation unit. The MAPD hydrogenation unit may be operable to contact at least a portion of the hydrogenated effluent from the acetylene hydrogenation unit with a second hydrogenation catalyst to produce a MAPD hydrogenated effluent.

According to one embodiment presently described, a method for operating an integrated system for producing olefins may include contacting a hydrogenation feed with a first hydrogenation catalyst to produce a hydrogenated effluent. The hydrogenation feed may include at least a portion of a first process effluent from a first olefin production process and at least a portion of a second process effluent from a second olefin production process. The hydrogenation feed may include at least hydrogen, ethylene, carbon monoxide, acetylene, methyl acetylene, and propadiene. The first hydrogenation catalyst has a temperature operating range of at least 40 degrees Celsius. The temperature operating range may be a difference between a runaway temperature and a cleanup temperature at a given hydrogenation feed composition, where the runaway temperature is the temperature at which 3% of ethylene in the hydrogenation feed is reacted and the cleanup temperature is the temperature at which the acetylene concentration in the hydrogenated effluent is equal to a threshold acetylene concentration. The hydrogenated effluent may include methyl acetylene (MA), propadiene (PD), or both. The method may further include contacting at least a portion of the hydrogenated effluent with a second hydrogenation catalyst. The contacting may cause hydrogenation of at least a portion of the methyl acetylene, propadiene, or both, from the hydrogenated effluent to produce an MAPD hydrogenated effluent having a reduced concentration of methyl acetylene, propadiene, or both compared to the portion of the hydrogenated effluent prior to contact with the second hydrogenation catalyst.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
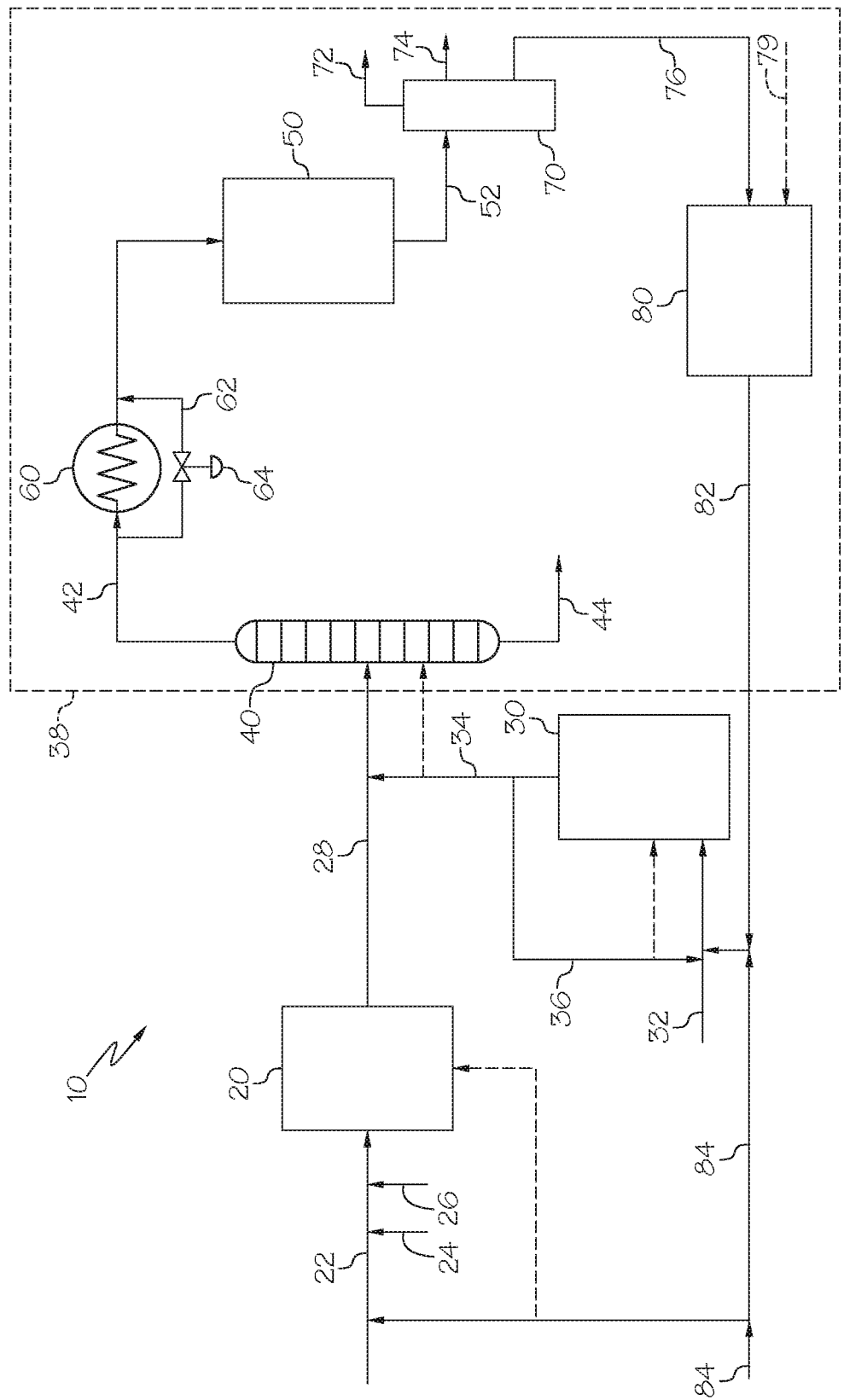
FIG. 1 schematically depicts an integrated process for producing olefins that includes an FCDh system integrated with a steam cracking system and a shared effluent processing system, according to one or more embodiments shown and described herein.

It should be understood that the drawings are schematic in nature, and may not include some components of reactor systems commonly employed in the art, such as, without limitation, sensors, temperature transmitters, pressure transmitters, flow meters, pumps, valves, heat exchangers, internal reactor structures, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

One or more embodiments of the present disclosure are directed to systems and methods for operating integrated processes for producing olefins that include a plurality of olefin production processes utilizing a common effluent processing system to purify and separate the plurality of effluent streams from the olefin production processes. In particular, one or more embodiments of the present disclosure are directed to systems and methods for operating integrated processes for producing olefins that may reduce or prevent thermal runaway of the acetylene hydrogenation unit in response to a sudden decrease in carbon monoxide (CO) concentration in the hydrogenation feed caused by the sudden decrease and/or loss of flow of the effluent stream from one of the olefin production processes. In some embodiments of the present disclosure, the methods for operating an integrated system for producing olefins may include contacting a hydrogenation feed with a first hydrogenation catalyst to produce a hydrogenated effluent. The hydrogenation feed may include at least a portion of a first process effluent from a first olefin production process and at least a portion of a second process effluent from a second olefin production process. The hydrogenation feed may include at least hydrogen, ethylene, carbon monoxide, acetylene, methyl acetylene, and propadiene. The first hydrogenation catalyst may be a hydrogenation catalyst having a temperature operating range of at least 40° C., the temperature operating range being a difference between a runaway temperature and a cleanup temperature at a given hydrogenation feed composition, wherein the runaway temperature is the temperature at which 3% of ethylene in the hydrogenation feed is reacted, and the cleanup temperature is the temperature at which the acetylene concentration in the hydrogenated effluent is equal to a threshold acetylene concentration set by a downstream user or customer, such as equal to 1 ppm or other threshold acetylene concentration set by the downstream users/customers. The hydrogenated effluent may include methyl acetylene (MA), propadiene (PD), or both (MAPD). The method may further include contacting at least a portion of the hydrogenated effluent with a second hydrogenation catalyst, wherein the contacting causes hydrogenation of at least a portion of the methyl acetylene, propadiene, or both from the hydrogenated effluent to produce an MAPD hydrogenated effluent.

Contacting the hydrogenation feed with the first hydrogenation catalyst having a wide temperature operating range for a given hydrogenation feed composition may reduce the response of the acetylene hydrogenation unit to a sudden decrease in CO concentration due to a sudden decrease or complete loss of flow of one of the first or second olefin production processes of the integrated system for producing olefins, thereby reducing or preventing thermal runaway of the acetylene hydrogenation unit. Additionally, contacting at least a portion of the hydrogenated effluent with the second hydrogenation catalyst downstream of the acetylene hydrogenation unit may reduce the concentration of MA and PD below a threshold MAPD concentration to produce the MAPD hydrogenated effluent, which may be recycled back to the first or second olefin production process. Reducing the MAPD concentration in the MAPD hydrogenated effluent may reduce coke formation in the first or second olefin production process.

Described herein is an example of an integrated process for producing olefins that includes steam cracking combined with FCDh and utilizing a single shared effluent processing system having an acetylene hydrogenation unit. The integrated process is utilized to provide context for the methods of operating the acetylene hydrogenation unit presently disclosed, which may reduce or prevent breakthrough of acetylene to downstream processes. It should be understood that the schematic diagrams of FIGS. 1-4, 6, and 7 are only example systems, and that other systems suitable for producing olefins are contemplated herein, and the concepts described herein may be utilized in such alternate systems. For example, the concepts described herein may be equally applied to other integrated systems with alternate reactor units and regeneration units, such as those that operate under non-fluidized conditions or are downers rather than risers. Additionally, the presently described methods and processes for processing a chemical stream in a reactor system should not be limited only to embodiments for reactor systems designed to produce light olefins through steam cracking integrated with fluidized catalytic dehydrogenation, such as the reactor system described with respect to FIG. 1, as other processes for producing olefins (e.g., utilizing different feedstocks) are contemplated. Other processes for producing olefins, such as but not limited to methanol-to-olefin processes and dehydration processes, may also be included in the integrated system in place or in addition to one or both of the steam cracking unit or the FCDh system.

The systems and methods for operating the integrated system for producing olefins will now be discussed in further detail with reference to FIG. 1. The chemical stream that is processed may be referred to as a feed stream or simply a feed, which is processed by a reaction, separation, or other process to form a product stream, reactor effluent, or just effluent. The feed may comprise a composition, and depending upon the feed composition, an appropriate catalyst may be utilized to convert the contents of the feed into an effluent that may include light olefins or other chemical products.

As used herein, "start-up" may generally refer to the time when reactor temperature, reactor pressure, flow rates (e.g., flow rates of feed gas to the reactor (hydrocarbon and/or inert gases), fuel gas and air for catalyst regeneration, gas for catalyst stripping and fluidization, oxygen-containing gas for oxygen treating the catalyst, etc.), catalyst recirculation rates, or combinations of these are being established but have not yet reached the desired values for stable operation for the given reaction.

As used herein, "shut-down" may generally refer to the time when the temperatures, pressures, flow rates, and/or catalyst recirculation rates of the reactor system (e.g., reactor and/or regenerator) are being reduced prior to the end of the process reaction.

As used herein, the term "system recycle" may refer to operation of a reactor system in which at least a portion of the reactor effluent (e.g., FCDh effluent) may be recycled back to the hydrocarbon feed or directly back to the reactor. System recycle may be part of normal operation, such as when one or more streams from the effluent processing system are recycled back to one or more olefin production processes in order to increase the yield of olefins. Additionally, system recycle events may include off-spec products events in which the reactor system is operated in a system recycle mode until the reactor effluent and/or operating conditions of the reactor are returned back to target or normal operating conditions. The reactor system may also be operated in system recycle mode in response to planned or unplanned interruptions in operation of other reactor systems, such as disruptions in operation of the steam cracking system, integrated with the reactor system disclosed herein. In some embodiments, system recycle may result in the temperature of the reactor decreasing to a low temperature (i.e., <550° C.). In other circumstances, system recycle may include circulating an inert gas through the reactor to maintain the catalyst in a fluidized state.

As used herein, "unit trip" may refer to conditions when a reactor unit completely shuts down, or conditions in which temperatures are reduced, and/or flow rates of one or more streams are reduced or bypassed due to, for example, runaway conditions during chemical processing. Unit trip may include different levels of unit trips, such as severe unit trips in which the entire reactor system is completely shut-down, or a mid-level trip in which the temperature is reduced, the pressure is reduced, or one or more streams are bypassed. Low-temperature reaction conditions, such as those present during start-up, shut-down, system recycle, or unit trip and conditions in which inert gases are circulated through the reactor system without hydrocarbon feed streams may be referred to as non-normal operating conditions herein. Normal operating conditions refer to high temperature, steady state conditions such as temperatures above 550° C. or those suitable for catalytic reaction of a given reactant.

As used herein, the term "hydrogenation feed" may refer to an effluent from the separation system passed to the acetylene hydrogenation unit that includes at least 95% by mass of the acetylene from the cracked gas introduced to the separation system.

As used herein, the term "acetylene-depleted stream" may refer to another effluent stream from the separation system that is different than the hydrogenation feed and includes less than 5% by mass of the acetylene from the cracked gas passed to the separation system.

As used herein, the terms "upstream" and "downstream" are relative to the direction of flow of materials through the integrated process. For example, a first unit operation is upstream of a second unit operation if one or more material streams flow from the first unit operation to the second unit operation. The first unit operation is downstream of the second unit operation if one or more material streams flow from the second unit operation to the first unit operation.

As used herein, the term "selectivity" may refer to a ratio of the moles of a desired product to moles of all the products in a reactor effluent with all the products normalized to the same carbon number. For example, ethylene selectivity of the acetylene hydrogenation unit may be a ratio of the moles of additionally produced ethylene in the hydrogenated effluent divided by the total moles of all the products produced during the hydrogenation reaction. For example, if all acetylene is converted to ethylene, the selectivity is 100%. If all acetylene is converted to ethane, the selectivity is 0 (zero). If all the acetylene and also some of incoming ethylene is converted to ethane, the selectivity then becomes negative.

As used herein, the term "breakthrough" may refer to passing of a specific reactant, such as but not limited to, acetylene, methyl acetylene, propadiene, or other compound, from one processing unit to another downstream processing unit in an amount greater than a threshold value specified by the olefin users, for example 1 parts per million by volume (ppmv). In an example, breakthrough may occur when the specific reactant undergoes substantially incomplete conversion in a reaction system so that an effluent passed out of the reaction system has a concentration of the specific reactant of greater than 1 ppmv, or greater than 2 ppmv depending on olefin users and the location.

As used herein, the term "threshold acetylene concentration" may refer to a concentration of acetylene in a hydrogenated effluent from the acetylene hydrogenation unit at or below which the concentration of acetylene is considered to be within the specifications for product purity provided by olefin users and/or does not cause fouling of catalysts or other disruptions in downstream processes.

As used herein, the term "thermal runaway" may refer to a condition of a process in which an incremental increase in temperature of the process changes the operating conditions in a manner that produces or generates heat, which further increases the temperature.

As used herein, the term "normal operating conditions" may refer to high temperature, steady state conditions such as temperatures suitable for catalytic reaction of a given reaction, such as a temperature suitable for conducting the acetylene hydrogenation reaction in the acetylene hydrogenation unit. A suitable temperature for a hydrogenation unit may be a temperature within the temperature operating range of a hydrogenation catalyst for a given composition.

As used herein, the term "temperature operating range" of a hydrogenation catalyst may refer to a difference between a runaway temperature and a clean-up temperature for a given system configuration at a given composition of the hydrogenation feed.

As used herein, the term "clean-up temperature" may refer to an operating temperature of the acetylene hydrogenation unit at which the acetylene concentration in the hydrogenated effluent is equal to a threshold acetylene concentration set by a downstream user or customer, for a given hydrogenation catalyst and at a given composition of the hydrogenation feed. For example, the clean-up temperature may be an operating temperature of the acetylene hydrogenation unit at which the acetylene concentration in the hydrogenated effluent is equal to 1 ppmv or other threshold acetylene concentration set by the downstream users and/or customers, for a given hydrogenation catalyst and at a given composition of the hydrogenation feed.

As used herein, the term "runaway temperature" may refer to an operating temperature of the acetylene hydrogenation unit at which 3% of the ethylene from the hydrogenation feed is reacted in the acetylene hydrogenation unit for a given hydrogenation catalyst and at a given composition of the hydrogenation feed.

Referring to FIG. 1, an integrated process 10 for producing olefins is schematically depicted. The integrated process 10 may include a steam cracking system 20, a fluidized catalytic cracking (FCDh) system 30, and an effluent processing system 38, which may be operable to process the effluents from the steam cracking system 20 and the FCDh system 30. The steam cracking system 20 may be operable to convert at least a portion of a first hydrocarbon feed 22 to produce a cracked gas 28 that includes at least hydrogen, carbon monoxide (CO), acetylene, and at least one steam cracker product. The FCDh system 30 may be operable to convert at least a portion of a second hydrocarbon feed 32 to produce an FCDh effluent 34 that includes at least hydrogen, CO, and at least one FCDh product. The cracked gas 28, or the cracked gas 28 and at least a portion of the FCDh effluent 34, may be passed to the effluent processing system 38, which may be operable to process the cracked gas 28 and/or the FCDh effluent 34 to produce one or more constituent streams, such as an ethylene stream 72, a propylene stream 74, a propane stream 76, or other constituent streams (not shown). The effluent processing system 38 may include at least a first separation system 40, an acetylene hydrogenation unit 50 downstream of the first separation system 40, a heat exchanger 60 disposed between the first separation system 40 and the acetylene hydrogenation unit 50, a second separation system 70 downstream of the acetylene hydrogenation unit 50, and an MAPD hydrogenation unit 80. The effluent processing system 38 may also include additional separation and/or purification processes (not shown) disposed downstream of the acetylene hydrogenation unit 50.

Figure 2:
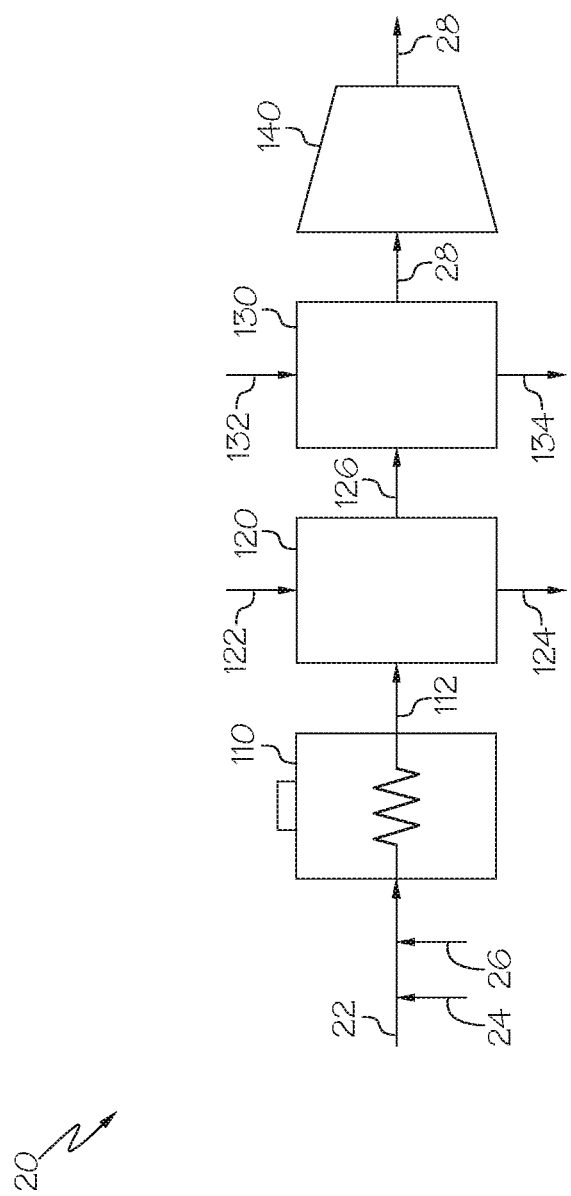
FIG. 2 schematically depicts the steam cracking system of the integrated process of FIG. 1, according to one or more embodiments shown and described herein.

Referring to FIG. 2, an embodiment of a steam cracking system 20 is schematically depicted. The steam cracking system 20 may include a steam cracking unit 110 and one or more of an oil quench unit 120, a water quench unit 130, a compressor system 140, or combinations of these. In some embodiments, the steam cracking system 20 may also include an acid gas removal unit (not shown). The first hydrocarbon feed 22 may be introduced to the steam cracking unit 110 for cracking one or more hydrocarbon constituents of the first hydrocarbon feed 22 to produce one or more olefins. The first hydrocarbon feed 22 may be any hydrocarbon stream, such as a product stream from a petrochemical process or naphtha from a refining operation for crude oil, natural gas liquids (NGL), or other hydrocarbon sources. In some embodiments, the first hydrocarbon feed 22 may include a plurality of different hydrocarbon streams combined prior to or in the steam cracking unit 110. In some embodiments, the first hydrocarbon feed 22 may be a light hydrocarbon feedstock, such as a feedstock including ethane, propane, butane, naphtha, other light hydrocarbon, or combinations of these.

The steam cracking unit 110 may be operable to receive the first hydrocarbon feed 22 and crack one or more constituents of the first hydrocarbon feed 22 to produce a cracker effluent 112. The steam cracking unit 110 may be operable to contact the first hydrocarbon feed 22 with steam at temperatures of from 500° C. to 850° C. to produce the cracker effluent 112. A sulfur-containing composition 24, a methanol-containing stream 26, or both, may also be introduced to the steam cracking unit 110. The sulfur-containing composition 24, the methanol-containing stream 26, or both, may be introduced directly into the steam cracking unit 110 or may be combined with the first hydrocarbon feed 22 upstream of the steam cracking unit 110. The sulfur-containing composition 24 may include one or more sulfur-containing compounds, such as, but not limited to dimethyl disulfide (DMDS), dimethyl sulfide (DMS), diethyl disulfide (DEDS), methyl mercaptan (MM), or combinations thereof. The sulfur-containing compounds from the sulfur-containing composition 24 may passivate the heating coil in the steam cracking furnace of the steam cracking unit 110 to manage the formation of coke in the steam cracking unit 110. Increasing or decreasing the sulfur-containing compounds may change an amount of CO generated in the steam cracking unit 110, thereby changing the CO concentration (e.g., amount of CO) in the cracker effluent 112.

Ethane, propane, naphtha, and other hydrocarbons present in the first hydrocarbon feed 22 may be steam cracked in the steam cracking unit 110 to produce at least one or more light olefins, such as but not limited to ethylene, propylene, butenes, or combinations of these. The steam cracking unit 110 may be operated under conditions (i.e., temperature, pressure, residence time, etc.) sufficient to produce one or more light olefins, such as ethylene and propylene, from the hydrocarbons in the first hydrocarbon feed 22. In some embodiments, the steam cracking unit 110 may be operated at a temperature of from 500° C., to 850° C., from 500° C. to 810° C., from 550° C. to 850° C., from 550° C. to 810° C., from 600° C. to 850° C., or from 600° C. to 810° C. The temperature of the steam cracking unit 110 may depend on the composition of the first hydrocarbon feed 22 introduced to the steam cracking unit 110. Other suitable operating conditions for hydrocarbon cracking processes are well known in the art.

The cracker effluent 112 may include one or more cracking reaction products, such as, but not limited to, ethylene, propylene, butenes (e.g., 1-butene, trans-2-butene, cis-2-butene, isobutene), ethane, propane, other light hydrocarbons, or combinations of these. The cracker effluent 112 can also include hydrogen, CO, acetylene, methyl acetylene, propadiene, methane, other compounds produced in the steam cracking unit 110, unreacted constituents of the first hydrocarbon feed 22, or combinations of these. For example, the cracking reactions in the steam cracking unit 110 may produce byproducts, such as hydrogen and carbon monoxide (CO), and side-reaction products, such as acetylene, methyl acetylene (MA), propadiene (PD), other side-reaction products, or combinations of these. Additionally, unreacted hydrocarbons and/or other constituents of the first hydrocarbon feed 22 may pass through the steam cracking unit 110 without undergoing reaction so that the cracker effluent 112 includes these unreacted constituents of the first hydrocarbon feed 22. Acid and alcohol gases may also be produced in the steam cracking unit 110.

Referring still to FIG. 2, the cracker effluent 112 may be passed from the steam cracking unit 110 to the oil quench unit 120 downstream of the steam cracking unit 110. The oil quench unit 120 may be operable to quench the cracker effluent 112 with a hydrocarbon quench liquid 122 to reduce the temperature of the cracker effluent 112 and remove heavy hydrocarbon constituents to produce an oil-quench effluent 126. The oil-quench effluent 126 may be passed from the oil quench unit 120 to the water quench unit 130 downstream of the oil quench unit 120. The water quench unit 130 may be operable to quench the cracker effluent 112 with liquid water to further reduce the temperature of the oil-quench effluent 126 and remove steam to produce the cracked gas 28. Although the water quench unit 130 is shown in FIG. 2 as being downstream of the oil quench unit 120, it is understood that the water quench unit 130 may alternatively be positioned upstream of the oil quench unit 120. The steam cracking system 20 may optionally include an acid gas removal system (not shown) for removing acid gases from the cracked gas 28. Alternatively, in some embodiments, the acid gas removal system may be incorporated into the effluent processing system 38 (FIG. 1). The cracked gas 28 may be passed to a compression system 140 operable to reduce the volume of cracked gas 28 upstream of the effluent processing system 38.

Figure 3:
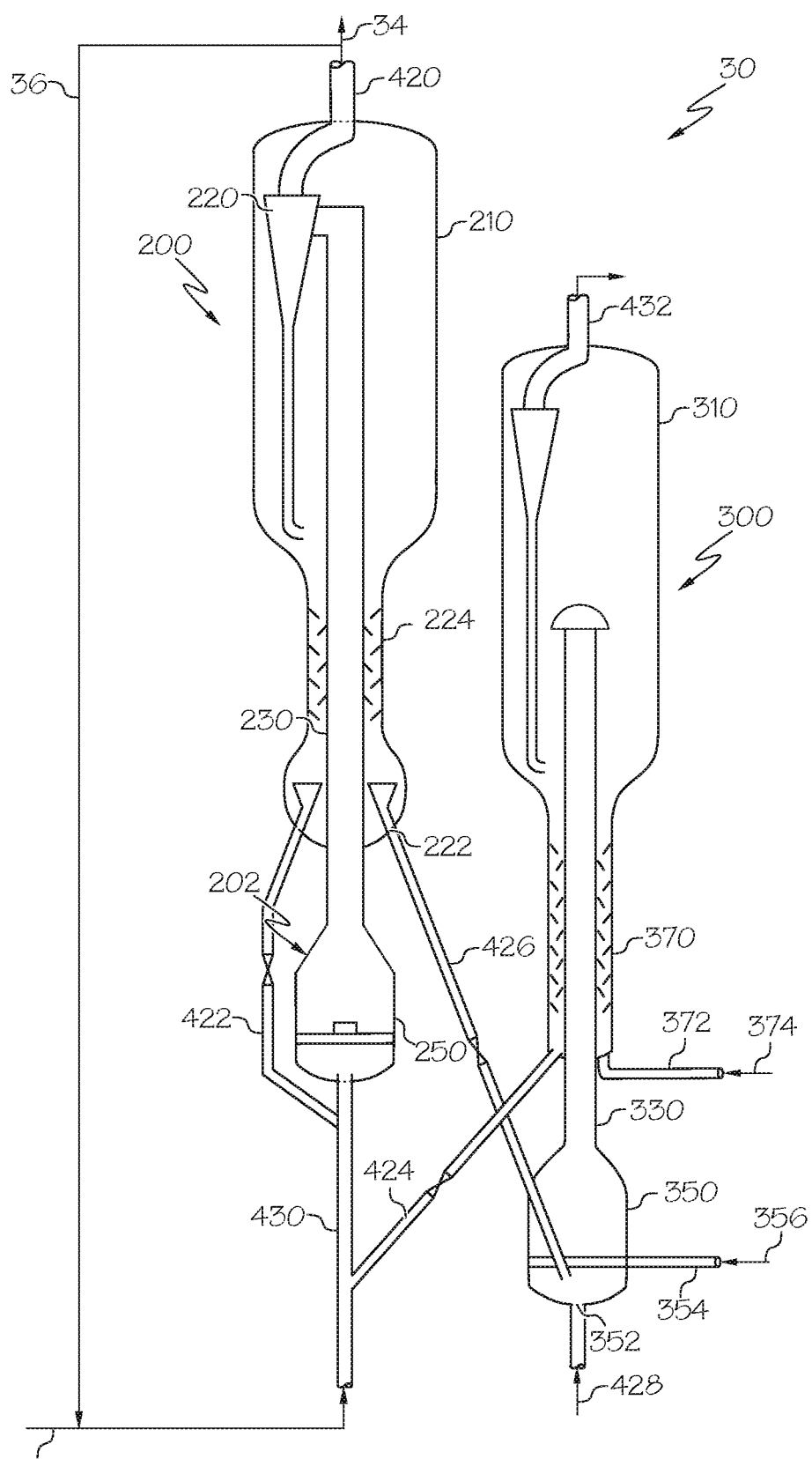
FIG. 3 schematically depicts the FCDh system of the integrated process of FIG. 1, according to one or more embodiments shown and described herein.

Referring now to FIG. 3, the FCDh system 30 may be operable to receive a second hydrocarbon feed 32 and contact the second hydrocarbon feed 32 with a dehydrogenation catalyst to produce an FCDh effluent 34. The second hydrocarbon feed 32 to the FCDh system 30 may include at least one of propane, n-butane, iso-butane, ethane, or ethylbenzene. The second hydrocarbon feed 32 may include one or more hydrocarbon streams from a hydrocarbon processing facility. The second hydrocarbon feed 32 may be the same as or different than the first hydrocarbon feed 22. In some embodiments, the second hydrocarbon feed 32 may include a propane or ethane stream (e.g., propane stream 76 in FIG. 1) recovered from the effluent processing system 38 and recycled back to the FCDh system 30. In the FCDh system 30, at least a portion of the second hydrocarbon feed 32 may be converted to light olefins or other products through dehydrogenation in the presence of a dehydrogenation catalyst. The dehydrogenation catalyst may be any catalyst known in the art for dehydrogenating hydrocarbons to produce olefins. The FCDh effluent 34 may include at least CO, hydrogen, and at least one FCDh product. The at least one FCDh product may include one or more of ethylene, propylene, or combinations thereof.

Referring to FIG. 3, an example FCDh system 30 is schematically depicted. The FCDh system 30 may include a reactor portion 200 and a catalyst processing portion 300. As used herein in the context of FIG. 3, the reactor portion 200 may refer to a portion of the FCDh system 30 in which the major process reaction takes place. For example, the second hydrocarbon feed 32 may be dehydrogenated in the presence of the dehydrogenation catalyst in the reactor portion 200 of the FCDh system 30. The reactor portion 200 comprises a reactor 202, which may include a downstream reactor section 230, an upstream reactor section 250, and a catalyst separation section 210, which serves to separate the catalyst from the chemical products formed in the reactor 202.

Also, as used herein, the catalyst processing portion 300 of the FCDh system 30 of FIG. 3 generally refers to the portion of the FCDh system 30 in which the catalyst is in some way processes—such as removal of coke deposits, heating of the catalyst, reactivating the catalyst, other processing operations, or combinations of these—during normal operation of the FCDh system 30. In some embodiments, the catalyst processing portion 300 may include a combustor 350, a riser 330, a catalyst separation section 310, and an oxygen treatment zone 370. The combustor 350 of the catalyst processing portion 300 may include one or more lower combustor inlet ports 352 and may be in fluid communication with the riser 330. The combustor 350 may be in fluid communication with the catalyst separation section 210 via transfer line 426, which may supply deactivated catalyst (during normal operating conditions) from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via transfer line 424 and transport riser 430), which may supply processed catalyst from the catalyst processing portion 300 back to the reactor portion 200. The combustor 350 may include the lower combustor inlet port 352 where air inlet 428 connects to the combustor 350. The air inlet 428 may supply air or other reactive gases, such as an oxygen-containing gas to the combustor 350. Air and/or other reactive gases, may be introduced to the combustor 350 to aid in combustion of a supplemental fuel. The combustor 350 may also include a fuel inlet 354. The fuel inlet 354 may supply a fuel, such as a hydrocarbon stream 356 to the combustor 350. The oxygen treatment zone 370 may include an oxygen-containing gas inlet 372, which may supply an oxygen-containing gas 374 to the oxygen treatment zone 370 for oxygen treatment of the catalyst.

Referring to FIG. 3, general operation of the FCDh system 30 to conduct a continuous reaction under normal operating conditions will be described. During operation of the reactor portion 200 of the FCDh system 30, the second hydrocarbon feed 32 may enter the transport riser 430, and FCDh effluent 34 may exit the FCDh system 30 via pipe 420. According to one or more embodiments, the FCDh system 30 may be operated by feeding the second hydrocarbon feed 32 and a fluidized dehydrogenation catalyst into the upstream reactor section 250. Hydrocarbons in the second hydrocarbon feed 32 may contact the dehydrogenation catalyst in the upstream reactor section 250, and each may flow upwardly into and through the downstream reactor section 230 to produce at least one FCDh product under normal operating conditions.

The FCDh effluent 34 and the dehydrogenation catalyst may be passed out of the downstream reactor section 230 to a separation device 220 in the catalyst separation section 210. The FCDh effluent 34 may include hydrogen, CO, and at least one FCDh product. The FCDh effluent 34 may also include unreacted portions of the second hydrocarbon feed 32, fluidization gases, byproducts, reaction intermediates, other gases, or combinations of these. The at least one FCDh product may include ethylene, propylene, or other light olefins. The FCDh effluent 34 may have a CO concentration greater than the concentration of CO in the cracked gas 28 from the steam cracking system 20. The FCDh effluent 34 may have a concentration of CO of from 500 parts per million by volume (ppmv) to 2400 ppmv, such as from 1000 ppmv to 2000 ppmv. The FCDh effluent 34 may include acetylene, methyl acetylene (MA), propadiene (PD), or combinations of these. A concentration of acetylene in the FCDh effluent 34 may be less than 50 ppmv. A concentration of MA in the FCDh effluent 34 may be less than or equal to 300 ppmv. A concentration of PD in the FCDh effluent 34 may be less than or equal to 100 ppmv.

The dehydrogenation catalyst may be separated from the FCDh effluent 34 in the separation device 220. The FCDh effluent 34 may then be transported out of the catalyst separation section 210. For example, the separated vapors of the FCDh effluent 34 may be removed from the FCDh system 30 via a pipe 420 at a gas outlet port of the catalyst separation section 210. In some embodiments, the separation device 220 may be a cyclonic separation system, which may include two or more stages of cyclonic separation.

According to some embodiments, following separation from vapors of the FCDh effluent 34 in the separation device 220, the dehydrogenation catalyst may generally move through the stripper 224 to the reactor catalyst outlet port 222 where the dehydrogenation catalyst may be transferred out of the reactor portion 200 via transfer line 426 and into the catalyst processing portion 300. Optionally, the dehydrogenation catalyst may also be transferred directly back into the upstream reactor section 250 via standpipe 422. In some embodiments, recycled dehydrogenation catalyst from the stripper 224 may be premixed with processed dehydrogenation catalyst from the catalyst processing portion 300 in the transport riser 430.

The separated dehydrogenation catalyst may be passed from the catalyst separation section 210 to the combustor 350 of the catalyst processing portion 300. The dehydrogenation catalyst may be processed in the catalyst processing portion 300 during normal operation to remove coke deposits, heat the catalyst, reactivate the catalyst, other catalyst processing, or any combinations of these. As previously discussed, processing the dehydrogenation catalyst in the catalyst processing portion 300 may include removing coke deposits from the catalyst, raising the temperature of the catalyst through combustion of a combustion fuel source, reactivating the catalyst, stripping one or more constituents from the catalyst, other processing operation, or combinations of these. In some embodiments, processing the dehydrogenation catalyst in the processing portion 300 may include combusting a combustion fuel source in the presence of the dehydrogenation catalyst in the combustor 350 to remove coke deposits and/or heat the dehydrogenation catalyst to produce a heated catalyst. The heated dehydrogenation catalyst may be separated from the combustion gases in the catalyst separation section 310.

In some embodiments, the heated dehydrogenation catalyst may then be reactivated by conducting an oxygen treatment of the heated dehydrogenation catalyst. The oxygen treatment may include exposing the heated dehydrogenation catalyst to an oxygen-containing gas 374 for a period of time sufficient to reactivate the dehydrogenation catalyst. The oxygen treatment to reactivate the dehydrogenation catalyst may be conducted after combustion of the supplemental fuel to heat the dehydrogenation catalyst. The oxygen treatment may include treating the heated dehydrogenation catalyst with the oxygen-containing gas 374 for a period of at least two minutes, which may reactivate the dehydrogenation catalyst to produce a reactivated dehydrogenation catalyst. The oxygen-containing gas 374 may include an oxygen content of from 5 mole % to 100 mole % based on total molar flow rate of the oxygen-containing gas 374. In some embodiments, the oxygen treatment of the dehydrogenation catalyst may include maintaining the dehydrogenation catalyst at a temperature of at least 660° C. while exposing the dehydrogenation catalyst to a flow of the oxygen-containing gas 374 for a period of time greater than two minutes and sufficient to produce a reactivated dehydrogenation catalyst having a catalytic activity that is greater than the heated dehydrogenation catalyst after being heated by combustion of the supplemental fuel. The oxygen treatment may be conducted in the oxygen treatment zone 370, which may be downstream of the catalyst separation section 310 of the catalyst processing portion 300.

The combustion gases from combustion of coke and/or the supplemental fuel during processing of the dehydrogenation catalyst or other gases introduced to the dehydrogenation catalyst during catalyst processing and catalyst reactivation may be removed from the catalyst processing portion 300 via a regenerator effluent outlet 432.

FIG. 3 and the preceding discussion present one embodiment of a system for catalytically dehydrogenating hydrocarbons to produce light olefins. However, it is understood that other reactor system configurations may be employed for catalytic dehydrogenation of hydrocarbons to produce light olefins without departing from the scope of the present disclosure. For example, in some embodiments, the FCDh system 30 may include any type of fluidized reactor system operable to contact the second hydrocarbon feed 32 with a catalyst in a fluidization regime, such as bubbling regime, slug flow regime, turbulent regime, fast fluidization regime, pneumatic conveying regime, or combinations thereof.

Referring again to FIG. 3, the FCDh system 30 may be operated in system recycle in which at least a portion of the FCDh effluent 34 is recycled back to the reactor portion 200 of the FCDh system 30. The FCDh system 30 may be operated in system recycle mode during start-up of the FCDh system 30 or in response to an off-spec event in which the composition of the FCDh effluent 34 does not conform to the product stream target standards. In these situations, the FCDh effluent 34 may be recycled back to the FCDh system 30 while adjustments are made to the FCDh system 30 to bring the composition of the FCDh effluent 34 back into conformance. System recycle may also occur when the reactor system is integrated with another reactor system (e.g., such as the steam cracking system 20) and the other reactor system experiences an interruption (e.g., planned events such as planned maintenance or unplanned events such unexpected failures of equipment such as furnace, compressors, or other equipment). During system recycle operation, at least a portion of or all of the FCDh effluent 34 may be recycled back to the FCDh system 30 in an FCDh effluent recycle 36. The FCDh effluent recycle 36 may be combined with the second hydrocarbon feed 32 upstream of the transport riser 430 as shown in FIG. 3. In some embodiments, the FCDh effluent recycle 36 may be passed directly to the transport riser 430, in which the FCDh effluent recycle 36 is then combined with the second hydrocarbon feed 32 and the dehydrogenation catalyst.

Although the integrated system 10 is described herein in conjunction with FIG. 1 as integrating a steam cracking system 20 and an FCDh system 30, it is contemplated that other processes for producing olefins may be included in the integrated system 10 in addition to or as an alternative to the steam cracking system 20 or the FCDh system 30. Examples of other olefin production systems that may be included in the integrated system may include methanol-to-olefin processes, alcohol dehydration processes, or other olefin production processes.

Figure 4:
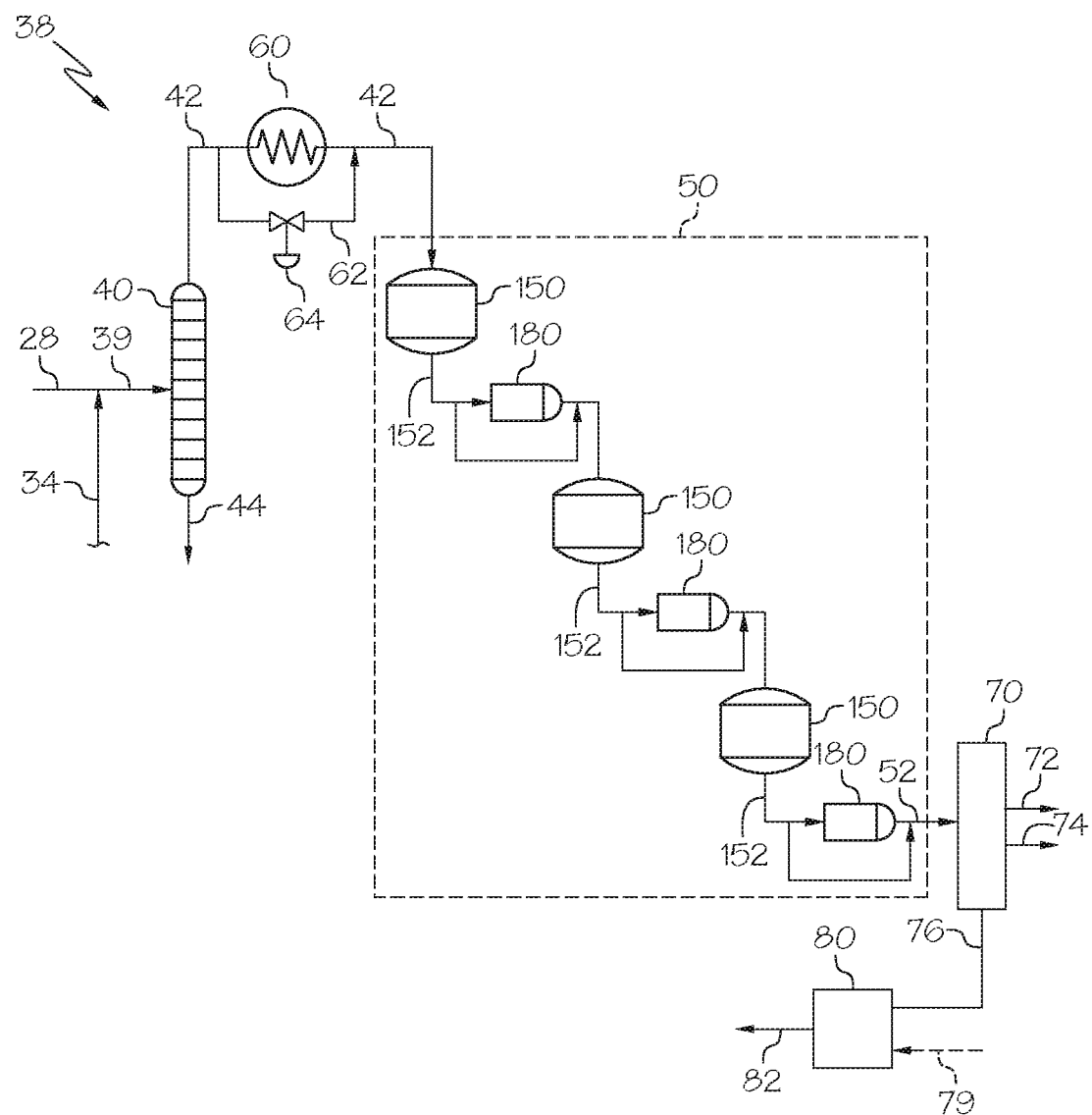
FIG. 4 schematically depicts a portion of the product processing system of the integrated process of FIG. 1, according to one or more embodiments shown and described herein.

Referring to FIG. 4, as previously discussed, the effluent processing system 38 may include at least the first separation system 40, the acetylene hydrogenation unit 50 downstream of the first separation system 40, the heat exchanger 60 disposed between the first separation system 40 and the acetylene hydrogenation unit 50, the second separation system 70, and the MAPD hydrogenation unit 80. The cracked gas 28, at least a portion of the FCDh effluent 34, or both may be passed to the first separation system 40. In some embodiments, the cracked gas 28 and the FCDh effluent 34 may be independently passed directly to the first separation system 40. In some embodiments, the cracked gas 28 and the FCDh effluent 34 may be combined upstream of the first separation system 40 and passed as a combined stream 39. The FCDh effluent 34 may be combined with the cracked gas 28 at any point downstream of the water quench unit 130 and oil quench unit 120 of the steam cracking system 20.

The first separation system 40 may be operable to produce at least the hydrogenation feed 42 and an acetylene-depleted stream 44 from the cracked gas 28, the portion of the FCDh effluent 34, or both. The first separation system 40 may include one or a plurality of separation units. The first separation system 40 may include any type of separation units operable to produce the hydrogenation feed 42 from the cracked gas 28, the FCDh effluent 34, or both. In some embodiments, the first separation system 40 may include a distillation unit in which the cracked gas 28, the FCDh effluent 34, or both may be separated into the hydrogenation feed 42 and the acetylene-depleted stream 44 by differences in boiling point temperatures of the constituents. In some embodiments, the first separation system 40 may be a multiple-stage distillation column. Separation of the constituents of the cracked gas 28, the FCDh effluent 34, or both by difference in boiling point temperature may include initially cooling the cracked gas 28, the FCDh effluent 34, or both to temperatures less than the boiling point temperatures of one or more constituents. Thus, the first separation system 40 may include a condenser (not shown) operable to condense one or more constituents of the cracked gas 28, the FCDh effluent 34, or both upstream of the distillation unit. The first separation system 40 is not limited to a distillation process. It is understood that other methods and processes for producing the hydrogenation feed 42 from the cracked gas 28, the FCDh effluent 34, or both are contemplated.

As previously discussed, the hydrogenation feed 42 may include at least 95% by weight of the acetylene from the cracked gas 28 passed to the first separation system 40. The hydrogenation feed 42 may include saturated and unsaturated hydrocarbons, such as, but not limited to, ethylene ($C_2H_4$), propylene ($C_3H_6$), acetylene ($C_2H_2$), methyl acetylene ($H_3C-C\equiv CH$), propadiene ($H_2C=C=CH_2$), methane ($CH_4$), ethane ($C_2H_6$), propane ($C_3H_8$), or combinations of these. The hydrogenation feed 42 may also include non-hydrocarbon gases, such as, but not limited to, hydrogen, CO, carbon dioxide ($CO_2$), inert gases, or combinations of these. Inert gases may include nitrogen, argon, or other inert gases present in the steam cracking system 20, the FCDh system 30, or both. In some embodiments, the hydrogenation feed 42 may include at least acetylene, hydrogen, CO, MA, and PD. The hydrogenation feed 42 may include at least 95%, or even at least 99% of the CO from the cracked gas and the portion of the FCDh effluent passed to the first separation system 40. The hydrogenation feed 42 may also include one or more product olefins, which may include but are not limited to propylene, ethylene, or combinations of these. The hydrogenation feed 42 may also include other hydrocarbons, such as but not limited to methane, ethane, propane, or combinations of these.

The acetylene-depleted stream 44 may include less than 5% by weight of the acetylene from the cracked gas 28. The acetylene-depleted stream 44 may include a greater weight percentage of higher boiling point hydrocarbons compared to the hydrogenation feed 42. These higher boiling point hydrocarbons may include saturated and unsaturated hydrocarbons, such as, but not limited to butane, butenes, butadiene, pentane, or other higher boiling temperature hydrocarbons.

The first separation system 40 may be a depropanizer for a front end configuration steam cracking system (FEDP). When the first separation system 40 is configured as an FEDP, the hydrogenation feed 42 may include C3 and C3− hydrocarbons and non-hydrocarbon gases. The C3 and C3− hydrocarbons may include, but are not limited to, methane, ethane, propane, ethylene, propylene, acetylene, methyl acetylene, propadiene, and combinations of these. The light gases in the hydrogenation feed 42 may include hydrogen, CO, carbon dioxide, nitrogen, or other non-hydrocarbon gases. When the first separation system 40 is an FEDP, the acetylene-depleted stream 44 may include C4 and C4+ hydrocarbons, such as butane, butenes, butadiene, pentane, pentenes (i.e., one or more of the various isomers of pentene), and other C4 and C4+ hydrocarbons. When the first separation system 40 is an FEDP, the hydrogenation feed 42 may have at least 95% of the acetylene, MA, and PD from the cracked gas 28 and the portion of the FCDh effluent 34. Further information on various front end configurations for acetylene hydrogenation in olefin production processes can be found in "Overview on C2 and C3 Selective Hydrogenation in Ethylene Plants" by Edgar L. Mohundro, 15th Ethylene Produces Conference, 2003 AICHE Spring National Meeting, New Orleans, La., the entire contents of which are incorporated herein by reference.

Referring to FIG. 4, the effluent processing system 38 may include the acetylene hydrogenation unit 50 downstream of the first separation system 40. The acetylene hydrogenation unit 50 may be positioned to receive the hydrogenation feed 42 from the first separation system 40. The hydrogenation feed 42 may be passed from the first separation system 40 to the acetylene hydrogenation unit 50.

The hydrogenation feed 42 may be contacted with the first hydrogenation catalyst in the acetylene hydrogenation unit 50. The contacting of the hydrogenation feed 42 with the first hydrogenation catalyst may cause hydrogenation of at least a portion of the acetylene in the hydrogenation feed 42 to produce the hydrogenated effluent 52, which may have a reduced concentration of acetylene compared to the hydrogenation feed 42. The hydrogenated effluent 52 may include reaction products from the hydrogenation reaction and unreacted constituents of the hydrogenation feed 42. The acetylene hydrogenation unit 50 may include one or a plurality of hydrogenation reactors, such as 1, 2, 3, or more than 3 hydrogenation reactors. The hydrogenation reactors of the acetylene hydrogenation unit 50 may be fixed bed reactors comprising a fixed bed of the first hydrogenation catalyst. The hydrogenation reactors of the acetylene hydrogenation unit 50 may be vapor phase reactors operable to conduct the hydrogenation reaction through contact of the first hydrogenation catalyst (a solid) with reactants in the vapor phase.

Referring to FIG. 4, in some embodiments, the acetylene hydrogenation unit 50 may include a plurality of hydrogenation reactors arranged in series (e.g., first hydrogenation reactor 150, second hydrogenation reactor 160, and third hydrogenation reactor 170). Referring to FIG. 4, in one embodiment, the acetylene hydrogenation unit 50 may include at least a first hydrogenation reactor 150 and a second hydrogenation reactor 160 downstream of the first hydrogenation reactor 150. The acetylene hydrogenation unit 50 may also include a third hydrogenation reactor 170 downstream of the second hydrogenation reactor 160. Typically, the first hydrogenation reactor 150 removes a majority of acetylene in the hydrogenation feed, while the second reactor 160 removes the rest of acetylene and the third reactor 170 acts as a polishing bed to prevent the hydrogenated effluent from being out-of-specification for acetylene concentration. The acetylene hydrogenation unit 50 may also, optionally, include heat exchangers 180 disposed between each of the hydrogenation reactors. Each of the heat exchangers 180 may be positioned downstream of one of the hydrogenation reactors 150, 160, 170 and may be operable to remove heat generated from the exothermic hydrogenation reaction in each hydrogenation reactor 150, 160, 170.

The hydrogenation feed 42 may be passed to the first hydrogenation reactor 150, which may be operable to hydrogenate at least acetylene from the hydrogenation feed 42 to produce a first hydrogenated effluent 152. The first hydrogenated effluent 152 may have a concentration of acetylene less than the concentration of acetylene in the hydrogenation feed 42. The first hydrogenation reactor 150 may have an acetylene conversion of greater than or equal to 85%, greater than or equal to 90%, or greater than or equal to 95% during normal operating conditions of the acetylene hydrogenation unit 50 in order to maintain the concentration of acetylene in the hydrogenated effluent 52 less than the threshold acetylene concentration. Heat may be removed from the first hydrogenated effluent 152 by passing the first hydrogenated effluent 152 through a heat exchanger 180. The first hydrogenated effluent 152 may be passed on the to the second hydrogenation reactor 160, which may be operable to further hydrogenate acetylene in the first hydrogenated effluent 152 to produce a second hydrogenated effluent 162. Heat may be removed from the second hydrogenated effluent 162 by passing the second hydrogenated effluent 162 through a heat exchanger 180. The second hydrogenated effluent 162 may be passed on the to the third hydrogenation reactor 170, which may be operable to further hydrogenate acetylene in the second hydrogenated effluent 162 to produce a third hydrogenated effluent 172. Heat may be removed from the third hydrogenated effluent 172 by passing the third hydrogenated effluent 172 through a heat exchanger 180. The third hydrogenated effluent 172 may be passed out of the acetylene hydrogenation unit 50 as the hydrogenated effluent 52.

Although not depicted in the figures, the acetylene hydrogenation unit 50 may include one or a plurality of temperature sensors, pressure sensors, flow meters, or combinations of these for measuring the temperature, pressure, or gas flow rates at one or a plurality of positions of the acetylene hydrogenation unit 50. The temperature, pressure, and/or gas flow rate may be determined for one or more of the plurality of acetylene hydrogenation reactors of the acetylene hydrogenation unit 50 and/or for the hydrogenation feed 42 introduced to the acetylene hydrogenation unit 50. The method of operating the acetylene hydrogenation unit 50 may include determining the temperature of the acetylene hydrogenation unit 50, a temperature of the hydrogenation feed 42 passed to the acetylene hydrogenation unit 50, or both.

The acetylene hydrogenation unit 50 may also include one or a plurality of analyzers, such as GC analyzers, operable to measure the concentration of CO, hydrogen, or other constituents in the hydrogenation feed 42, the hydrogenated effluent 52, intermediate effluents from one or more of the hydrogenation reactors of the acetylene hydrogenation unit 50, or combinations of these. In some embodiments, the stream for composition analysis may be retrieved from the hydrogenation feed 42 before introducing the hydrogenation feed 42 to the acetylene hydrogenation unit 50. Alternatively or additionally, the stream for composition analysis may be retrieved from the hydrogenated effluent 52 passed out of the acetylene hydrogenation unit 50. In some embodiments, the stream for composition analysis may be retrieved from one or more intermediate effluent streams passed of one of the hydrogenation reactors of the acetylene hydrogenation unit 50. The method of operating the acetylene hydrogenation unit 50 may include determining the concentration of CO, hydrogen, or other constituent in the acetylene hydrogenation unit 50.

The acetylene hydrogenation unit 50 can be operated at conditions under which the catalytic hydrogenation is selective for hydrogenation of acetylene over hydrogenation of propylene and ethylene. The first hydrogenation catalyst may be an acetylene hydrogenation catalyst that is a catalyst selective for hydrogenating acetylene relative to product compounds in the hydrogenation feed 42. The acetylene hydrogenation unit 50 may be operated at a temperature sufficient to hydrogenate acetylene at a conversion rate that prevents breakthrough of acetylene to downstream processes, but less than a temperature resulting in increased hydrogenation of olefins and thermal runaway of the acetylene hydrogenation unit 50. The operating temperature of the acetylene hydrogenation unit 50 may be from 10° C. to 200° C., such as from 10° C. to 100° C., although the operating temperature of the acetylene hydrogenation unit 50 may depend on the composition of the hydrogenation feed 42, as will be discussed in further detail herein. Other factors influencing the operating temperature of the acetylene hydrogenation unit 50 may include, but are not limited to, the type of hydrogenation catalyst, the age/activity of the hydrogenation catalyst, flow rate, inlet acetylene concentration, CO concentration, presence of contaminants or poisons, other factors, or combinations of these. The acetylene hydrogenation unit 50 may operate at a pressure of from 100 pounds per square inch gauge (psig) to 1000 psig (i.e., about 690 kilopascals (kPa) to about 6900 kPa). The acetylene hydrogenation unit 50 may additionally operate at a gas hourly space velocity (GHSV) of from 1,000 to 14,000 (volume per volume of catalyst per hour).

When operating under normal operation conditions, a conversion of acetylene in the first hydrogenation reactor 150 of the acetylene hydrogenation unit 50 may be sufficient to maintain a concentration of acetylene in the hydrogenated effluent 52 less than or equal to the threshold acetylene concentration. In some embodiments, the acetylene conversion in the first hydrogenation reactor 150 may be greater than or equal to 85% under normal operation conditions, such as greater than or equal to 88%, greater than or equal to 90%, or even greater than or equal to 95%. Normal operation conditions refer to operation of the acetylene hydrogenation unit 50 at steady state with the acetylene concentration in the hydrogenated effluent 52 less than or equal to the threshold acetylene concentration. In some embodiments, under normal operation conditions, the acetylene conversion in the first hydrogenation reactor 150 may be from 85% to 95%, or from 88% to 92%.

The hydrogenated effluent 52 may refer to the effluents or compositions passed out of the acetylene hydrogenation unit 50, such as out of the last hydrogenation reactor of the acetylene hydrogenation unit 50. The hydrogenated effluent 52 may have an acetylene concentration less than the acetylene concentration of the hydrogenation feed 42. The hydrogenated effluent 52 may have an acetylene concentration of less than or equal to the threshold acetylene concentration, which may be specified by the downstream olefin product user or customer. In some embodiments, the hydrogenated effluent 52 may have an acetylene concentration of less than or equal to 2 part per million by volume (ppmv), less than or equal to 1 ppmv, less than or equal to 0.5 ppmv, or even less than or equal to 0.1 ppmv. The first hydrogenation catalyst and operating conditions of the acetylene hydrogenation unit 50 may be selective for hydrogenating acetylene relative to hydrogenation of product compounds, such as propylene and ethylene, produced in the steam cracking system 20 and/or the FCDh system 30.

Referring again to FIG. 4, the effluent processing system 38 may include a heat exchanger 60 disposed between the first separation system 40 and the acetylene hydrogenation unit 50. The heat exchanger 60 may include the bypass 62 having a control valve 64. The temperature of the hydrogenation feed 42 at the inlet of the acetylene hydrogenation unit 50 may be increased or decreased by controlling the amount of the hydrogenation feed 42 passing through the heat exchanger 60 and the amount of the hydrogenation feed 42 bypassing the heat exchanger 60 through the bypass 62. Controlling an amount of the hydrogenation feed 42 bypassed around the heat exchanger 60 may allow for increasing or decreasing the temperature of the hydrogenation feed 42 at the inlet of the acetylene hydrogenation unit 50. The heat exchanger 60 for the hydrogenation feed 42 may be any type of heat exchanger known in the chemical industry.

The hydrogenated effluent 52 may be passed to a second separation system 70. The second separation system 70 may include one or a plurality of unit operations operable to separate the hydrogenated effluent 52 into a plurality of constituent streams, such as but not limited to, an ethylene stream 72, a propylene stream 74, a propane stream 76, other constituent stream, or combinations of these. The greatest portion (e.g., greater than 90%) of the MAPD from the hydrogenated effluent 52 may be included in the propane stream 76 passed out of the second separation system 70. One or more of the constituent streams may be passed to one or more unit operations and/or processes downstream of the second separation system 70 for further processing of the hydrogenated effluent 52 or as a product stream. Downstream processes may include vapor compression, separation, drying, or other operations and processes. One or more of the constituent streams may be passed as reactants or raw materials to further production processes, such as polymer production processes. In some embodiments, the propane stream 76 or other constituent stream may be passed or recycled back to the steam cracking system 20 and/or the FCDh system 30 as at least a portion of the first hydrocarbon feed 22 and/or the second hydrocarbon feed 32, respectively.

Figure 5:
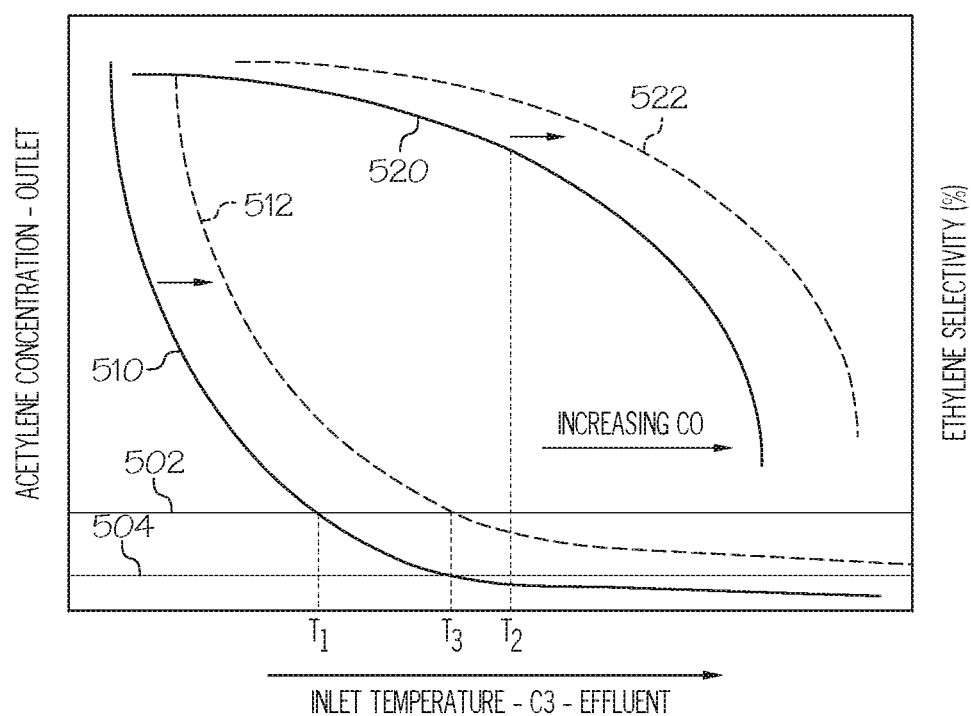
FIG. 5 graphically depicts a concentration of acetylene (y-axis-left) and an ethylene selectivity (y-axis-right) for an acetylene hydrogenation unit as a function of a temperature (x-axis) of a hydrogenation feed passed to the acetylene hydrogenation unit, according to one or more embodiments shown and described herein.

Referring now to FIG. 5, the acetylene concentration in the hydrogenated effluent 52 (y-axis left) and the ethylene selectivity of the acetylene hydrogenation unit 50 (y-axis right) are depicted as functions of the temperature (x-axis) of the hydrogenation feed 42 at the inlet to the acetylene hydrogenation unit 50. Line 502 in FIG. 5 represents a threshold acetylene concentration for the hydrogenated effluent 52, below which the concentration the acetylene may be considered reduced to a level sufficient to satisfy the requirements of olefin users and/or to prevent or reduce fouling of catalysts, out-of-specification product streams, or other issues in downstream processes. As shown in FIG. 5, the acetylene concentration (curve 510) in the hydrogenated effluent 52 decreases with increasing inlet temperature for a given composition of the hydrogenation feed 42. FIG. 5 shows that the acetylene concentration 510 in the hydrogenated effluent 52 can be increased or decreased by decreasing or increasing, respectively, the inlet temperature to the acetylene hydrogenation unit 50. Temperature $T_1$ for the given composition of the hydrogenation feed 42 for curve 510 can be defined as the lowest temperature at which the acetylene concentration in the hydrogenated effluent 52 is equal to or less than the threshold acetylene concentration 502. At temperatures of the hydrogenation feed 42 greater than $T_1$ the acetylene concentration (510) in the hydrogenated effluent 52 is less than the threshold acetylene concentration. For temperatures of the hydrogenation feed 42 less than $T_1$, the acetylene concentration (510) in the hydrogenated effluent 52 may be greater than the threshold acetylene concentration. Temperature $T_1$ in FIG. 5 may be considered the cleanup temperature of a particular catalyst for a given composition of the hydrogenation feed.

FIG. 5 also shows the ethylene selectivity of the acetylene hydrogenation unit 50 (curve 520) as a function of inlet temperature for the same composition of the hydrogenation feed 42 as curve 510. As shown in FIG. 5, the ethylene selectivity (curve 520) decreases with increasing inlet temperature. Thus, as the inlet temperature to the acetylene hydrogenation unit 50 increases, the ethylene selectivity of the acetylene hydrogenation unit 50 decreases, indicating that more acetylene and/or even some ethylene is converted to ethylene, which may be caused by increased hydrogenation of ethylene in the acetylene hydrogenation unit 50. Increased hydrogenation of ethylene may lead to thermal runaway. For example, at temperatures of the hydrogenation feed 42 greater than temperature $T_2$, the ethylene selectivity may decrease to a point at which an unacceptable amount of ethylene undergoes hydrogenation. For Example, temperature $T_2$ may be the runaway temperature at which 3% of the ethylene from the hydrogenation feed 42 is reacted in the acetylene hydrogenation unit 50.

Since the ethylene hydrogenation reaction is exothermic, additional heat from the increased hydrogenation of ethylene and other olefins is released and may further increase the temperature in the acetylene hydrogenation unit 50, which further shifts the hydrogenation reaction towards hydrogenation of ethylene and propylene. The increasing heat generated from increasing hydrogenation of ethylene and other olefins may lead to thermal runaway of the acetylene hydrogenation unit 50. As previously discussed, the increased temperatures in excess of 200° C. experienced during thermal runaway can trip the acetylene hydrogenation unit, requiring restart of the system. Additionally, the increased temperatures in excess of 200° C. can damage the hydrogenation catalyst and equipment, such as reactors, instruments, heat exchangers, and other equipment, and may increase safety risks. In many runaway situations, severe loss of catalyst performance resulting from thermal runaway can require catalyst replacement which leads to significant unit down time. Thermal runaway can also result in increased loss of olefin products through over-hydrogenation of the ethylene and propylene.

Referring again to FIG. 5, a temperature operating window for the acetylene hydrogenation unit 50 for a given composition of the hydrogenation feed 42 can be defined between the cleanup temperature (e.g., temperature $T_1$ in FIG. 5, below which the acetylene concentration in the hydrogenated effluent 52 is greater than the threshold acetylene concentration 502) and the runaway temperature (e.g., temperature $T_2$, above which the ethylene selectivity decreases and hydrogenation of olefin products can result in thermal runaway of the acetylene hydrogenation unit 50).

Changes in the CO concentration of the hydrogenation feed 42 may change the operating window of the acetylene hydrogenation unit 50. Increasing the CO concentration in the hydrogenation feed 42 may widen the process window and shift the process window for the temperature of the hydrogenation feed 42 towards greater temperatures. In FIG. 5, curve 512 may represent the acetylene concentration in the hydrogenated effluent 52 as a function of inlet temperature of the hydrogenation feed 42 for operation of the acetylene hydrogenation unit 50 with a greater concentration of CO, such as when the FCDh effluent is integrated into the product processing system 38, compared to the concentration of CO for curve 510 (e.g., when only the cracked gas 28 is passed to the product processing system 38). At a given temperature of the hydrogenation feed 42, increasing the concentration of CO reduces the conversion of acetylene. By increasing the concentration of CO in the acetylene hydrogenation unit 50, the inlet temperature $T_3$ at which the acetylene concentration in the hydrogenated effluent 52 is equal to the threshold acetylene concentration 502 is greater than the corresponding temperature $T_1$ of the hydrogenation feed 42 for curve 510 (having a lesser concentration of CO).

Increasing the CO concentration in the acetylene hydrogenation unit 50 may also shift the ethylene selectivity curve toward a higher inlet temperature. Referring to FIG. 5, curve 522 represents the ethylene selectivity for the acetylene hydrogenation unit 50 as a function of the inlet temperature of the hydrogenation feed for a greater CO concentration (e.g., such as when the FCDh effluent 34 is integrated into the product processing system 38) compared to the CO concentration for curve 520 (e.g., when only the cracked gas 28 is passed to the product processing system 38). As shown in FIG. 5, increasing the CO concentration (curve 522) in the acetylene hydrogenation unit 50 can increase the ethylene selectivity at a given temperature. This may enable operation of the acetylene hydrogenation unit 50 at greater inlet temperatures compared to operating the acetylene hydrogenation unit 50 with a lesser concentration of CO. However, a sudden decrease in the concentration of CO in the hydrogenation feed due to a sudden decrease or complete loss of flow of the FCDh effluent 34 may greatly increase the catalyst activity in the hydrogenation unit at the same temperature, not only potentially shifting the process to lower olefin selectivity, but also resulting in increased hydrogenation of olefin products, such as ethylene and/or propylene, which can lead to thermal runaway, as previously discussed herein.

Referring again to FIG. 1, the steam cracking system 20 and the FCDh system 30 may be integrated so that these processes share a common effluent processing system 38, which may include at least the first separation system 40, the acetylene hydrogenation unit 50, the second separation system 70, and the MAPD hydrogenation unit 80. The steam cracking system 20 can be operated, and the cracked gas 28 may be passed to the product processing system 38. The FCDh system 30 may also be operated, and at least a portion of the FCDh effluent 34 from the FCDh system 30 may be integrated into the product processing system 38. The portion of the FCDh effluent 34 may be integrated into the product processing system 38 by passing the portion of the FCDh effluent 34 to the first separation system 40, combining the portion of the FCDh effluent 34 with the cracked gas 28 upstream of the first separation system 40, or both. In some embodiments, the entire FCDh effluent 34 may be passed to the first separation system 40, combined with the cracked gas 28, or both. In some embodiments, only a portion of the FCDh effluent 34 may be passed to the first separation system 40, combined with the cracked gas 28, or both. The remaining FCDh effluent may be recycled back to the FCDh system 30 or back into combination with the second hydrocarbon feed 32 via FCDh effluent recycle 36. Additionally, in some embodiments, the portion of the FCDh effluent 34 passed to the first separation system 40, combined with the cracked gas 28, or both, may be a second portion of the FCDh effluent supplementing a first portion of the FCDh effluent already being passed into the product processing system 38.

As previously discussed, the concentration of CO in the FCDh effluent 34 may be greater than the concentration of CO in the cracked gas 28. The cracked gas 28 may have a concentration of CO of from 50 ppmv to 400 ppmv. The FCDh effluent 34 may have a concentration of CO of from 500 ppmv to 2400 ppmv, such as from 1000 ppmv to 2000 ppmv. When both the cracked gas 28 and the portion of the FCDh effluent 34 are passed to the effluent processing system 38, the amount of CO in the hydrogenation feed 42 may be greater than the amount of CO in the cracked gas 28.

Unit trip of the FCDh system 30 may cause a complete shutdown of the FCDh system 30 or recycle of a greater portion of the FCDh effluent 34 back to the FCDh system 30 through FCDh recycle 36. When this happens, the flow of the FCDh effluent 34 to the product processing system 38 may be suddenly reduced (e.g., through increased recycle back to the FCDh system 30) or eliminated (e.g., complete shutdown of the FCDh system 30 and sudden reduction of the flowrate of the FCDh effluent 34 to zero, or complete disconnection of FCDh system 30 with the effluent processing system 38). A sudden and substantial reduction in or complete loss of flow of the portion of the FCDh effluent 34 to the first separation system 40 (e.g., directly or in combination with the cracked gas 28) may result in a sudden decrease in the concentration of CO in the hydrogenation feed 42 to the acetylene hydrogenation unit 50.

As previously discussed, decreasing the concentration of CO in the hydrogenation feed 42, which decreases the CO concentration in the acetylene hydrogenation unit 50, may increase hydrogenation of ethylene and other olefin products in the acetylene hydrogenation unit 50, thereby decreasing the ethylene selectivity. The suddenly decreased concentration of CO in the hydrogenation feed 42 due to a sudden decrease or complete loss of flow of the FCDh effluent 34 to the effluent processing system 38 may increase activity of the hydrogenation catalyst and increase the reaction rate, at constant temperature, of the hydrogenation reaction of acetylene. The increased reaction rate may increase the hydrogenation of ethylene and other product olefins and reduce the ethylene selectivity. A sudden reduction in or complete loss of flow of the FCDh effluent 34 may also result in a sudden decrease the mass flow rate of the hydrogenation feed 42 and mass flow rate through the acetylene hydrogenation unit 50. This could lead to smaller gas hourly space velocity or residence time of the hydrogenation feed, which may also increase the hydrogenation of ethylene and other product olefins in the acetylene hydrogenation unit 50. As previously discussed, the increased hydrogenation of ethylene and other olefins in the acetylene hydrogenation unit 50 may lead to thermal runaway of the acetylene hydrogenation unit 50, which can reduce yields of product olefins and damage equipment and catalyst, as previously discussed herein.

The first hydrogenation catalyst in the acetylene hydrogenation unit 50 may be a hydrogenation catalyst that has reduced sensitivity to changes in CO concentration. For instance, the first hydrogenation catalyst may have a wide temperature operating range, which may reduce the sensitivity of the first hydrogenation catalyst to a sudden increase and/or decrease in CO concentration in the hydrogenation feed 42. The temperature operating range here may refer to the difference between the cleanup temperature and the runaway temperature for the acetylene hydrogenation unit 50 of the integrated process 10 comprising the cracking unit 20, FCDh unit 30, and a first separation system 40 having a front end depropanizer (FEDP) configuration. The wide temperature operating range of the first hydrogenation catalyst may allow the temperature in the acetylene hydrogenation unit 50 to increase to a greater extent in response to a sudden decrease in CO concentration without reaching the temperature at which at least 3% of the ethylene in the hydrogenation feed 42 is hydrogenated. In some embodiments, the first hydrogenation catalyst may have a temperature operating range sufficient to reduce or prevent thermal runaway of the acetylene hydrogenation unit 50 in response to a sudden loss of the flow of the FCDh effluent 34 from the FCDh system 30. In some embodiments, the first hydrogenation catalyst may have a temperature operating range greater than or equal to 40° C., greater than or equal to 45° C., or even greater than or equal to 50° C. for a given composition of the hydrogenation feed 42 when used in the acetylene hydrogenation unit 50 of the integrated system 10 in which the first separation system 40 has an FEDP configuration.

In some embodiments, the first hydrogenation catalyst can be a commercially-available Pd—Ag based selective hydrogenation catalyst with a broad temperature operating window. In some embodiments, the first hydrogenation catalyst may be an acetylene hydrogenation catalyst commercially-available for acetylene hydrogenation in an effluent processing system having a front-end de-ethanizer (FEDE) configuration. These types of selective hydrogenation catalysts with a broad temperature operating windows are not currently applied to selective hydrogenation for steam cracking units 20 and integrated processes 10 having a first separation system 40 with a front-end de-propanizer (FEDP) configuration due to insufficient activity for hydrogenating MAPD.

For steam cracking units 20 and integrated processes 10 having first separation systems 40 with a front-end deethanizer (FEDE) configuration, selective acetylene hydrogenation catalysts with broad temperature operating ranges are commercially-available as their activity is acceptable for acetylene removal when the hydrogenation feed 42 does not have a significant concentration of MAPD. In some embodiments, the first hydrogenation catalyst can be a selective hydrogenation catalyst for cracker systems which have an FEDP configuration or a selective hydrogenation catalyst for cracker systems which have an FEDE configuration.

Utilization of the first hydrogenation catalyst having a temperature operating range of greater than or equal to 40° C. may reduce or prevent thermal runaway of the acetylene hydrogenation unit 50 in response to a loss of flow of the FCDh effluent 34 from the FCDh system 30. However, the first hydrogenation catalyst with broad operation window may have reduced effectiveness for hydrogenating methyl acetylene (MA) and propadiene (PD) compared to other acetylene hydrogenation catalysts. Contacting the hydrogenation feed 42 with the first hydrogenation catalyst in the acetylene hydrogenation unit 50 may result in a conversion of MA in the acetylene hydrogenation unit 50 of less than or equal to 80%, such as less than or equal to 75%, less than or equal to 70%, less than or equal to 60%, or even less than or equal to 40%. Similarly, contacting the hydrogenation feed 42 with the first hydrogenation catalyst in the acetylene hydrogenation unit 50 may result in a conversion of PD in the acetylene hydrogenation unit 50 of less than or equal to 10%, such as less than or equal to 8%, less than or equal to 5%, or even less than or equal to 1%. The reduced conversion of MA and PD with the first hydrogenation compared to conventional hydrogenation catalysts does not pose a problem when the effluent processing system 38 has an FEDE configuration because, in the FEDE configuration, the first separation system 40 separates the MA and PD into the acetylene-depleted stream, which is not passed to the acetylene hydrogenation unit 50. Thus, with an FEDE configuration, the MA and PD are not passed to the acetylene hydrogenation unit 50. However, when effluent processing system 38 has an FEDP configuration, the first separation system 40 separates most of the MA and PD into the hydrogenation feed 42, which is then passed to the acetylene hydrogenation unit 50. When the first hydrogenation catalyst having a temperature operating range greater than or equal to 40° C. is used, the low conversion of MA and PD in the acetylene hydrogenation unit 50 may result in significant amounts of MA and PD in the hydrogenated effluent 52. The MAPD in the hydrogenated effluent 52 can result in increased production of coke when streams containing the MA and/or the PD are recycled back to an olefin production process, such as the FCDh system 30, or passed to downstream processes. Additionally, specifications from olefin users may require reduced concentrations of MA and PD below threshold concentrations for these compounds.

Referring again to FIG. 1, as previously discussed, the effluent processing system 38 may include the MAPD hydrogenation unit 80 downstream of the acetylene hydrogenation unit 50. The MAPD hydrogenation unit 80 may be operable to contact at least a portion of the hydrogenated effluent 52 with a second hydrogenation catalyst. The at least a portion of the hydrogenated effluent 52 passed to the MAPD hydrogenation unit 80 may have a combined concentration of MA and PD of less than or equal to 10 wt. %, such as less than or equal to 8 wt. %, or even less than or equal to 6 wt. %. The portion of the hydrogenated effluent 52 passed to the MAPD hydrogenation unit 80 may include, but is not limited to, one or more of propane, propylene, or combinations of these.

Contacting the portion of the hydrogenated effluent 52 with the second hydrogenation catalyst may be conducted in the presence of hydrogen. Contacting the portion of the hydrogenated effluent 52 with the second hydrogenation catalyst may hydrogenate at least a portion of the MA and PD in the portion of the hydrogenated effluent 52 to produce an MAPD hydrogenated effluent 82. In some embodiments, the portion of the hydrogenated effluent 52 passed to the MAPD hydrogenation unit 80 may include hydrogen. In other embodiments, a supplemental hydrogen stream 79 may be passed to the MAPD hydrogenation unit 80.

The MAPD hydrogenation unit 80 may include one or a plurality of MAPD hydrogenation reactors, such as 1, 2, 3, or more than 3 MAPD hydrogenation reactors. Each of the MAPD hydrogenation reactors may be a fixed bed reactor comprising a fixed bed of the second hydrogenation catalyst. The MAPD hydrogenation reactors of the MAPD hydrogenation unit 80 may be vapor phase reactors operable to conduct the hydrogenation reaction through contact of the second hydrogenation catalyst (a solid) with reactants in the vapor phase.

The second hydrogenation catalyst may be a catalyst operable to hydrogenate MA and PD. The second hydrogenation catalyst may be any commercially available hydrogenation catalyst effective to hydrogenate MA and PD to propylene, propane, or a combination of both. The second hydrogenation catalyst can be a conventional complete hydrogenation catalyst, such as but not limited to Ni, Pd, Pt, or Cu based supported catalyst, or combinations thereof. In some embodiments, the second hydrogenation catalyst is different from the first hydrogenation catalyst. The MAPD hydrogenation unit 80 may be operated under conditions sufficient to hydrogenate at least a portion of the MA and PD from the hydrogenated effluent 52 (e.g., the MA/PD in the propane stream 76 from the second separation system 70) to produce the MA/PD depleted stream 82. The MAPD hydrogenation unit 80 may be operated at a temperature sufficient to hydrogenate MA/PD at a conversion rate that prevents breakthrough of MA/PD to downstream processes. The operating temperature of the MAPD hydrogenation unit 80 may be from 10° C. to 200° C., such as from 10° C. to 100° C., although the operating temperature of the MAPD hydrogenation unit 80 may depend on the composition of the portion of the hydrogenated effluent 52 passed to the MAPD hydrogenation unit 80. Other factors influencing the operating temperature of the MAPD hydrogenation unit 80 may include, but are not limited to, the type of second hydrogenation catalyst, the age/activity of the second hydrogenation catalyst, flow rate, inlet concentrations of MA and PD, presence of contaminants or poisons, other factors, or combinations of these. The MAPD hydrogenation unit 80 may operate at a pressure of from 100 pounds per square inch gauge (psig) to 1000 psig (i.e., about 690 kilopascals (kPa) to about 6900 kPa) with the second hydrogenation catalyst.

Referring to FIG. 1, in some embodiment, the portion of the hydrogenated effluent 52 passed to the MAPD hydrogenation unit 80 may include one or more effluent streams from the second separation system 70, such as the propane stream 76. The hydrogenated effluent 52 may be passed to the second separation system 70, which may be operable to separate the hydrogenated effluent 52 into at least the ethylene stream 72, the propylene stream 74, and the propane stream 76. The propane stream 76 may include the MA and PD and may be the portion of the hydrogenated effluent 52 passed to the MAPD hydrogenation unit 80. The MAPD hydrogenation unit 80 may be operable to contact the propane stream 76 with the second hydrogenation catalyst in the presence of hydrogen to hydrogenate at least a portion of the MA and PD from the propane stream 76 to produce the MAPD hydrogenated effluent 82. In some embodiments, the MAPD hydrogenated effluent 82 may be passed to the FCDh system 30 as a recycle propane stream, combined with the second hydrocarbon stream 32 upstream of the FCDh system 30, or both. In some embodiments, the MAPD hydrogenated effluent 82 may be combined with a supplemental hydrocarbon stream 84, such as a supplemental propane stream, upstream of the FCDh system 30 to produce a combined stream 86, which may be passed to the FCDh system 30 or combined with the second hydrocarbon feed 32 upstream of the FCDh system 30. In some embodiments, the second hydrocarbon feed 32 may be the supplemental hydrocarbon stream 84, and the MAPD hydrogenated effluent 82 may be combined therewith upstream of the FCDh system 30. As shown in FIG. 1, at least a portion of the supplemental hydrocarbon stream 84 may be passed to the steam cracking unit 20.

Figure 6:
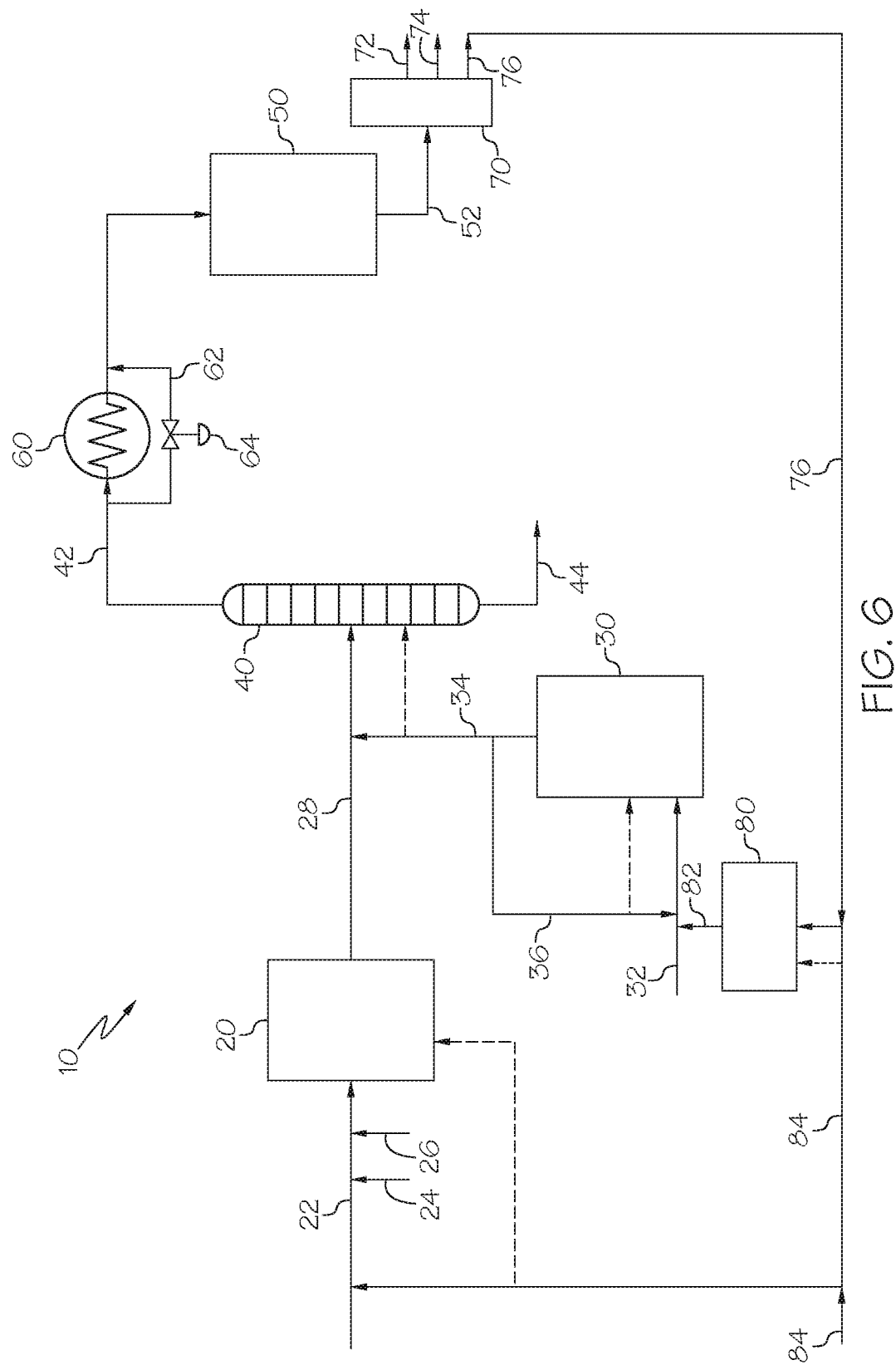
FIG. 6 schematically depicts another integrated process for producing olefins that includes an FCDh system integrated with a steam cracking system and a shared effluent processing system, according to one or more embodiments shown and described herein.

Referring now to FIG. 6, in some embodiments, the supplemental hydrocarbon stream 84 may also be passed to the MAPD hydrogenation unit 80 and contacted with the second hydrogenation catalyst before being passed to the FCDh system 30. Depending on the source of the supplemental hydrocarbon stream 84, the supplemental hydrocarbon stream 84 may include various unsaturated hydrocarbon compounds, which may include, but are not limited to various alkenes, alkynes, aromatic compounds, or combinations of these. In some embodiments, the supplemental hydrocarbon stream 84 may include MA, PD, or both. These unsaturated hydrocarbon impurities in the supplemental hydrocarbon stream 84 may produce coke in the FCDh system 30 at the operating conditions. The additional coke produced by unsaturated hydrocarbon impurities in the supplemental hydrocarbon stream 84 may reduce the activity of the catalyst in the FCDh system 30, thereby reducing the yield, selectivity, or both, of the FCDh system 30. The additional coke formation can also lead to operation difficulty longer term. Contacting the supplemental hydrocarbon stream 84 with the second hydrogenation catalyst in the MAPD hydrogenation unit 80 may hydrogenate at least a portion of the unsaturated hydrocarbon impurities in the supplemental hydrocarbon stream 84, thereby reducing the amount of unsaturated hydrocarbon impurities passed into the FCDh system 30.

Referring again to FIG. 6, in some embodiments, the supplemental hydrocarbon stream 84 may be combined with the at least a portion of the hydrogenated effluent 52 (e.g., propane stream 76) upstream of the MAPD hydrogenation unit 80. In other embodiments, the supplemental hydrocarbon stream 84 and the portion of the hydrogenated effluent 52 may be passed separately to the MAPD hydrogenation unit 80. The MAPD hydrogenated effluent 82 may then be passed from the MAPD hydrogenation unit 80 to the FCDh system 30. In some embodiments, the MAPD hydrogenated effluent 82 may be combined with the second hydrocarbon feed 32 upstream of the FCDh system 30 or may be passed to the FCDh system 30 separate from the second hydrocarbon feed 32. In some embodiments, the MAPD hydrogenated effluent 82 may be the second hydrocarbon feed 32 passed to the FCDh system 30.

In some embodiments, at least a portion of the supplemental hydrocarbon stream 84 may be passed to the steam cracking system 20. The portion of the supplemental hydrocarbon stream 84 may be combined with the first hydrocarbon feed 22 upstream of the steam cracking system 20 or may be passed separately to the steam cracking system 20. The portion of the supplemental hydrocarbon stream 84 may be passed to the steam cracking system 20 without passing through the MAPD hydrogenation unit 80.

Figure 7:
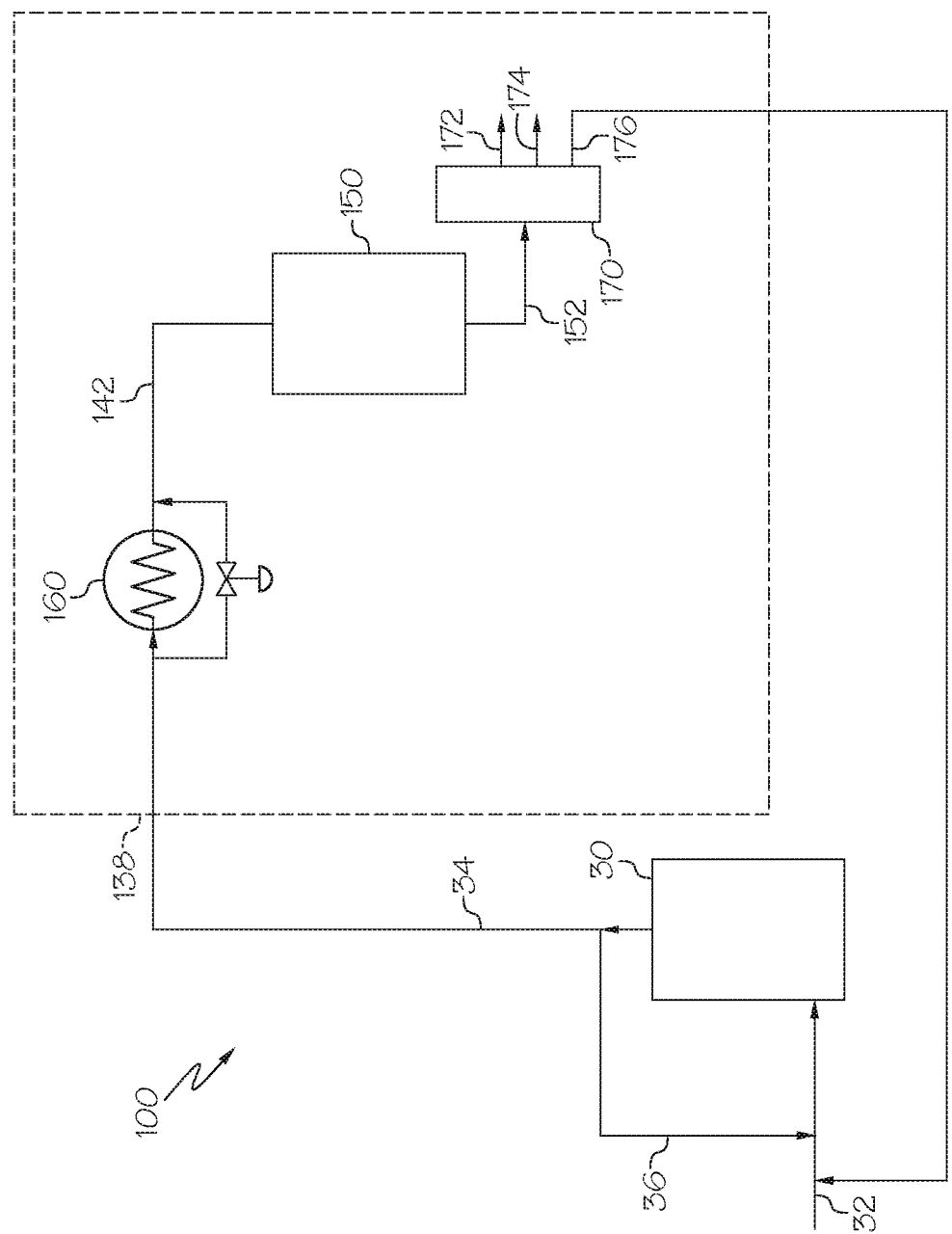
FIG. 7 schematically depicts a stand-alone FCDh system with a dedicated effluent processing system, according to one or more embodiments shown and described herein.

Referring now to FIG. 7, an FCDh olefin production process 100 is schematically depicted. The process depicted in FIG. 7 includes an FCDh system 30 with a dedicated effluent processing system 138 that is not integrated with a steam cracking system 20 or any other olefin production processes. In process 100, at least a portion of the FCDh effluent 34 from the FCDh system 30 may be passed to a hydrogenation unit 150 as the hydrogenation feed 142. The hydrogenation feed 142 may include at least CO, hydrogen, acetylene, MA, and PD. The hydrogenation feed 142 may additionally include olefin compounds and/or other gases. The hydrogenation feed 142 may have any of the compositions, constituents, or properties previously described herein for the hydrogenation feed 42. The hydrogenation feed 142 may be passed through a heat exchanger 160 and to the hydrogenation unit 150.

With a stand-alone FCDh process 100 in which the FCDh system 30 is not integrated with a steam cracking system 20, sudden changes in CO concentration of the hydrogenation feed 142 to the hydrogenation unit 150 are no longer an issue. For a stand-alone FCD process 100 having a dedicated effluent processing system 138, the hydrogenation unit 150 may include a third hydrogenation catalyst, which may be a high-severity selective hydrogenation catalyst that is selective for hydrogenating acetylene, MA, and PD. The third hydrogenation catalyst may include any commercially-available high-severity selective hydrogenation catalyst. The hydrogenation feed 142 may be contacted with the third hydrogenation catalyst in the hydrogenation unit 150 to produce a hydrogenated effluent 152. Contact of the hydrogenation feed 142 with the third hydrogenation catalyst may hydrogenate at least a portion of the acetylene, MA, and PD from the hydrogenation feed 142 to produce the hydrogenated effluent 152 having concentrations of acetylene, MA, and PD below threshold concentrations for these compounds.

The hydrogenated effluent 152 may be passed to the second separation system 170, which may be operable to separate the hydrogenated effluent 152 into a plurality of hydrocarbon steams, such as, but not limited to, an ethylene stream 172, a propylene stream 174, a propane stream 176, other streams, or combinations of these streams. Because a high-severity selective hydrogenation catalyst is able to be used, the dedicated effluent processing system 138 for the stand-alone FCDh process 100 may not include an additional hydrogenation unit to further remove MA and PD from the propane stream 176 before passing the propane stream 176 back to the FCDh system 30.

Referring again to FIG. 1, methods for operating an integrated system 10 for producing olefins may include contacting the hydrogenation feed 42 with the first hydrogenation catalyst to produce the hydrogenated effluent 52. The hydrogenation feed 42 may include at least a portion of a first process effluent from a first olefin production process and at least a portion of a second process effluent from a second olefin production process. The hydrogenation feed 42 may include at least hydrogen, ethylene, carbon monoxide, acetylene, methyl acetylene, and propadiene. The hydrogenation feed 42 may have any other compositions, properties, or characteristics previously described herein for the hydrogenation feed 42. In some embodiments, the hydrogenation feed 42 may include at least 95% of the CO from the first process effluent (e.g., cracked gas 28), the second process effluent (e.g., the portion of the FCDh effluent 34), or both. The first hydrogenation catalyst may include a hydrogenation catalyst having a temperature operating range of at least 40° C., the temperature range being a difference between a runaway temperature and a cleanup temperature at a given hydrogenation feed composition, wherein the runaway temperature is the temperature at which 3% of ethylene in the hydrogenation feed 42 is reacted and the cleanup temperature is the temperature at which the acetylene concentration in the hydrogenated effluent 52 is equal to 1 ppm or other threshold acetylene concentration set by a downstream olefin user or customer. The hydrogenated effluent 52 may include MA, PD, or both. The hydrogenated effluent 52 may have any other constituents, properties, or characteristics previously described herein for the hydrogenated effluent 52. The first hydrogenation catalyst having a temperature operating range of greater than or equal to 40° C. may reduce or prevent thermal runaway of the acetylene hydrogenation unit 50 in response to a disruption in flow of the first process effluent or the second process effluent.

The methods may further include contacting at least a portion of the hydrogenated effluent 52 with a second hydrogenation catalyst, wherein the contacting causes hydrogenation of at least a portion of the MA, PD, or both from the hydrogenated effluent 52 to produce an MAPD hydrogenated effluent 82. In some embodiments, a combined concentration of MA and PD in the portion of the hydrogenated effluent 52 contacted with the second hydrogenation catalyst may be less than or equal to 10 wt. %. The MAPD hydrogenated effluent 82 may have any of the compositions, properties, or characteristics previously discussed herein for the MAPD hydrogenated effluent 82.

Referring to FIG. 1, in some embodiments, the first process effluent may include the cracked gas 28 produced by cracking at least a portion of the first hydrocarbon feed 22 in the steam cracking system 20. The cracked gas 28 may include at least hydrogen, carbon monoxide, acetylene, methyl acetylene, and propadiene. In some embodiments, the second process effluent may include at least a portion of the FCDh effluent 34 produced by dehydrogenating at least a portion of the second hydrocarbon feed 32 in the FCDh system 30. The portion of the FCDh effluent 34 may include at least hydrogen and carbon monoxide. In some embodiments, the methods may include cracking at least a portion of the first hydrocarbon feed 22 in the steam cracking system 20 to produce the cracked gas 28 comprising at least hydrogen, carbon monoxide, acetylene, methyl acetylene, and propadiene. In some embodiments, the methods may further include dehydrogenating at least a portion of the second hydrocarbon feed 32 in the FCDh system 30 to produce the FCDh effluent 34 comprising at least hydrogen and carbon monoxide. The steam cracking system 20 and FCDh system 30 may have any of the features, characteristics, or operating conditions previously described herein for these systems. The first hydrocarbon feed 22, second hydrocarbon feed 32, cracked gas 28, and FCDh effluent 34 may have any of the compositions, properties, or characteristics previously described herein for these streams, respectively.

As previously discussed, the hydrogenation feed 42 may be contacted with the first hydrogenation catalyst in the acetylene hydrogenation unit 50. In some embodiments, the method may further include passing the hydrogenation feed 42 to the acetylene hydrogenation unit 50. In some embodiments, contact of the hydrogenation feed 42 with the first hydrogenation catalyst in the acetylene hydrogenation unit 50 may produce a conversion of MA from the hydrogenation feed 42 of less than 80%. In some embodiments, contact of the hydrogenation feed 42 with the first hydrogenation catalyst may produce a conversion of PD from the hydrogenation feed 42 of less than 10%.

Referring still to FIG. 1, in some embodiments, the methods may further include passing at least a portion of the MAPD hydrogenated effluent 82 to the FCDh system 30. In some embodiments, the MAPD hydrogenated effluent 82 may include a propane stream. In some embodiments, the methods may further include passing a supplemental hydrogen stream 79 to the MAPD hydrogenation unit 80. In some embodiments, the methods may further include combining at least a portion of the second hydrocarbon feed 32 with the portion of the hydrogenated effluent 52 (e.g., propane stream 76) before or during contacting of the portion of the hydrogenated effluent 52 with the second hydrogenation catalyst in the MAPD hydrogenation unit 80.

In some embodiments, the methods may further include separating the first process effluent and the second process effluent (e.g., the cracked gas 28 and the portion of the FCDh effluent 34) into the hydrogenation feed 42 and an acetylene-depleted stream 44. The first separation system 40 for separating the first process effluent and the second process effluent into the hydrogenation feed 42 and acetylene-depleted stream 44 may have FEDP configuration.

EXAMPLES

Embodiments of the present disclosure will be further clarified by the following examples, which should not be construed as limiting on the disclosed and/or claimed embodiments presently described.

Example 1: Production and Analysis of FCDh Effluent

In Example 1, an FCDh effluent was produced and analyzed for composition with respect to C3+ compounds and C3− compounds. The propane dehydrogenation was carried out in a modified Davison Circulating Riser (DCR) pilot unit, in which in-situ fuel combustion is carried out in the regeneration section. Approximately 4100 grams of a supported Ga—Pt catalyst was loaded in the circulating system and about 90 g of the catalyst was calculated to be in the reactor at any given time. The inlet temperature to the riser (reactor) was controlled at 630° C. and the pressure was set to a gauge pressure of 90 kilopascals (kPa) (13 psig or absolute pressure of 191 kPa/27.7 psia). High purity propane was injected into the system to achieve a weight hourly space velocity (WHSV) of propane around 3.5 per hour. Nitrogen ($N_2$) was co-fed into the system mostly as a carrier gas of catalyst. The partial pressure of propane was around a gauge pressure of about 30 kPa (4.3 psig). The temperature for catalyst regeneration ranged between 700° C. and 750° C. High purity methane ($CH_4$) was used as the fuel gas in the regenerator and was injected at rate of 50 standard liters per hour.

The reactor system was operated for a period of time sufficient to attain steady state operation, at which point samples of the FCDh effluent from the reactor system were collected and analyzed for composition using an on-line Maxum GC. In particular, the FCDh effluents were analyzed to determine the concentrations of CO, carbon dioxide ($CO_2$), $C_2$ and $C_{2-}$ compounds (including hydrogen), and $C_3$ compounds. The results are provided below in Table 1.

TABLE 1

Composition of FCDh Effluent of Example 1

| Fuel Gas in Regenerator | High-purity $CH_4$ |
|---|---|
| CO (ppmv) | 1178 |
| CO2 (ppmv) | 88 |
| $C_2$, $C_{2-}$, & $H_2$ (mol %) | 30.6 |
| $C_3$ (mol %) | 69.3 |

The data shows that the concentration of CO in the FCDh effluent can be much greater than the concentration of CO in a typical hydrogenation feed to the acetylene hydrogenation unit, the hydrogenation feed comprising only the cracked gas from a steam cracking system. The typical concentrations for CO in the hydrogenation feed when only the cracked gas is introduced to the separator is provided in Table 2 for a front end de-ethanizer (FEDE) configuration and a front end de-propanizer (FEDP) configuration. Additionally, the concentration of acetylene in the FCDh effluent was less than 50 ppmv and the concentrations of methyl acetylene (MA), and propadiene (PD) in the FCDh effluent (not listed in Table 1) were less than 300 ppmv and less than 100 ppmv, respectively.

The amounts of these highly unsaturated molecules contributed by the FCDh effluent were, therefore, found to be substantially less than the amounts of acetylene, MA, and PD contributed by the cracked gas from the steam cracking system. The following Table 2 provides the typical concentrations of acetylene and MA/PD in the hydrogenation feed when only the cracked gas is introduced to the first separation system. Table 2 provides data for a front end de-ethanizer (FEDE) and a front end de-propanizer (FEDP) configuration.

TABLE 2

Comparison of Compositions of the Hydrogenation Feed for FEDE and FEDP Configurations

| Configuration | CO in Hydrogenation Feed (ppmv) | Acetylene in Hydrogenation Feed (ppmv) | MA/PD in Hydrogenation Feed (ppmv) |
|---|---|---|---|
| FEDE | 50-200 | 1500-3000 | N/A |
| FEDP | 50-400 | 2000-5000 | 200-6000 |

Experimental Setup for Conducting the Selective Hydrogenation Reactions for Examples 2-4 and Comparative Examples 5-7

In the following examples and comparative examples, the selective hydrogenations of a hydrogenation feed comprising acetylene, MA, and PD were conducted in an isothermal acetylene hydrogenation unit with two identical ½ inch inside diameter reactors operated in parallel (first reactor and second reactor). 30 to 40 grams of hydrogenation catalyst were placed in each of the first reactor and second reactor. Each of the first reactor and second reactor included 10 evenly distributed thermocouples to monitor the temperature profile and determine whether isothermal temperature distribution conditions were achieved. Nitrogen was used as the internal standard, and methane ($CH_4$) was used as a balanced gas.

The composition for the hydrocarbon feed from the cracker unit obtained with a first separation system having an FEDP configuration is provided below in Table 3.

TABLE 3

Composition of C3/C3– Portion of the Cracked Gas for Examples 2-4 and Comparative Examples 5-7

| Feed Component | Concentration |
|---|---|
| Hydrogen (mol %) | 20 |
| CO (ppmv) | Variable* |
| $CH_4$ (mol %) | 30 |
| Acetylene (ppmv) | 3000 |
| C2 ($C_2H_4$ and $C_2H_6$) (mol %) | 38 |
| MA (ppmv) | 550 |
| PD (ppmv) | 410 |
| C3 ($C_3H_6$ and $C_3H_8$) (mol %) | 11.0 |

*The concentration of CO in the cracked gas is varied from 100 to 370 ppmv in the Examples and Comparative Examples.

The overall GHSV for acetylene hydrogenation unit is 5000 $hr^{-1}$ without the FCDh effluent. The composition for the FCDh effluent of Example 1 is used as the composition for the FCDh effluent. For simplicity the CO concentration in the hydrogenation feed from the FCDh effluent was made 1200 ppm. Acetylene, MA, and PD contributed by the FCDh effluent was not included due to its relatively low level compared to the amounts contributed by the cracked gas.

Examples 2 Through 4: Hydrogenation of Hydrogenation Feed Using a First Hydrogenation Catalyst having a Wide Temperature Operating Range In Examples 2 through 4, the hydrogenation of the hydrogenation feed (Table 3) was conducted using the first hydrogenation catalyst having a wide temperature operating range greater than 40° C. (Catalyst A). The temperature operating range of the first hydrogenation catalyst depends on the composition of the hydrogenation feed. The temperature operating range for each catalyst with each composition of the hydrogenation feed is provided below in Table 4. In Example 2, the hydrogenation feed included only the constituents contributed by the cracked gas. The composition for the hydrogenation feed in Example 2 is provided above in Table 3. For Example 3, the hydrogenation feed was determined based on a flow ratio of 2:1, where the flow ratio is the ratio of the amount of C3/C3– constituents contributed by the cracked gas to the amount of the C3/C3– constituents contributed by the FCDh effluent. For Example 4, the hydrogenation feed was determined based on a flow ratio of 12:1. For Examples 3 and 4, unit trip of the FCDh system was simulated by eliminating the constituents contributed by the FCDh system.

For each of Examples 2-4, the reactor system was operated for a period of time sufficient to attain steady state operation, at which point samples of the hydrogenated effluent from the reactor system were collected and analyzed for composition using techniques known in the art. In particular, the hydrogenated effluents were analyzed for composition, and the ethylene selectivity, the MA conversion, and the PD conversion were determined. Additionally, the clean-up temperature and temperature operating range of the first hydrogenation catalyst were determined for each hydrogenation feed composition of Examples 2-4. For Examples 3 and 4, the change in the delta T (ΔT) of the reactor upon the simulated unit trip of the FCDh system was determined. The ethylene selectivity, MA conversion, PD conversion, clean-up temperatures, temperature operating range for the first hydrogenation catalyst, and change in delta T for the reactor for each of Examples 2-4 are provided in Table 4.

Comparative Examples 5 Through 7:
Hydrogenation of Hydrogenation Feed Using a
Conventional Hydrogenation Catalyst In Comparative Examples 5 through 7, the hydrogenation of the hydrogenation feed was conducted using a conventional hydrogenation catalyst (Catalyst B). The temperature operating range of the first hydrogenation catalyst depends on the composition of the hydrogenation feed. The temperature operating range for each catalyst with each composition of the hydrogenation feed is provided below in Table 4. In Comparative Example 5, the hydrogenation feed included only the C3/C3− constituents contributed by the cracked gas. The composition for the hydrogenation feed of Comparative perature and temperature operating range for the conventional hydrogenation catalyst were determined for each hydrogenation feed composition of Comparative Examples 5-7. For each of Comparative Examples 6 and 7, the change in the delta T of the reactor upon the simulated unit trip of the FCDh system was determined. The ethylene selectivity, MA conversion, PD conversion, clean-up temperatures, temperature operating range for the conventional hydrogenation catalyst, and change in delta T for the reactor for each of Comparative Examples 5-7 are provided in Table 4.

Comparison of Examples 2-4 to Comparative
Examples 5-7

Table 4 provides the ethylene selectivity, MA conversion, PD conversion, clean-up temperatures, temperature operating range for the catalysts, and change in delta T for the reactor for each of Examples 2-4 and Comparative Examples 5-7.

TABLE 4

Ethylene Selectivity, MA Conversion, and PD Conversion
for Examples 2-4 and Comparative Examples 5-7

| # | Catalyst | Flow Ratio* | CO in hydrogenation feed (ppmv) | MA conc (ppmv) | PD Conc (ppmv) |
|---|---|---|---|---|---|
| Ex. 2 | A | (cracked gas portion only) | 100 | 550 | 410 |
| Ex. 3 | A | 2:1 | 370 | 410 | 310 |
| Ex. 4 | A | 12:1 | 160 | 520 | 390 |
| Comp. Ex. 5 | B | (cracked gas portion only) | 100 | 550 | 410 |
| Comp. Ex. 6 | B | 2:1 | 370 | 410 | 310 |
| Comp. Ex. 7 | B | 12:1 | 160 | 520 | 390 |

| # | Catalyst | Reactor Inlet Temperature | | T Op. Range (° C.) | At Clean-up Temperature | | | ΔT |
|---|---|---|---|---|---|---|---|---|
| | | Clean-Up Temp. (° C.) | Runaway Temp. (° C.) | | $C_2H_4$ Selectivity (%) | MA Conv (%) | PD Conv (%) | |
| Ex. 2 | A | 50 | >100 | >80 | 98 | 42 | 0 | — |
| Ex. 3 | A | 72 | >100 | >60 | 95 | 77 | 0 | <1 |
| Ex. 4 | A | 60 | >100 | >70 | 97 | 65 | 1 | <1 |
| Comp. Ex. 5 | B | 35 | 68 | 33 | 65 | 93 | 17 | — |
| Comp. Ex. 6 | B | 42 | 75 | 33 | 72 | 88 | 3 | 10.2 |
| Comp. Ex. 7 | B | 38 | 71 | 33 | 64 | 92 | 13 | <3 |

*As previously discussed herein, the flow ratio is the ratio of the amount of C3/C3− constituents contributed by the cracked gas to the amount of the C3/C3− constituents contributed by the FCDh effluent Example 5 is provided above in Table 3. For Comparative Example 6, the hydrogenation feed was determined based on a flow ratio of 2:1, and for Comparative Example 7, the hydrogenation feed was determined based on a flow ratio of 12:1. For Comparative Examples 6 and 7, unit trip of the FCDh system was simulated by eliminating the constituents contributed by the FCDh system.

For each of Comparative Examples 5-7, the reactor system was operated for a period of time sufficient to attain steady state operation, at which point samples of the hydrogenated effluent from the reactor system were collected and analyzed for composition using GC. In particular, the hydrogenated effluents were analyzed for composition, and the ethylene selectivity, the MA conversion, and the PD conversion were determined. Additionally, the clean-up tem- As shown in Table 4 above, Catalyst A, which was the first hydrogenation catalyst, had a substantially greater temperature operating range compared to Catalyst B. The results in Table 4 also show that Catalyst A having the greater temperature operating range resulted in a change in delta T of the reactor less than 1 in response to a simulated unit trip of the FCDh system. This change in delta T for Catalyst A was less than the change in delta T for Catalyst B of Comparative Examples 6 and 7 in response to the simulated unit trip of the FCDh system. This indicates that Catalyst A may be less sensitive to changes in CO concentration and may reduce or prevent the chances of thermal runaway of the acetylene hydrogenation reactor in response to a sudden loss of flow of the FCDh effluent, such as during unit trip of the FCDh system. Catalyst A of Examples 2-4 also resulted in a greater ethylene selectivity compared to Catalyst B of Comparative Examples 5-7.

Table 4 also shows that Catalyst A having the greater temperature operating range may provide lower conversions of MA and PD. Thus, an additional hydrogenation step, such as passing a portion of the hydrogenated effluent to an MAPD hydrogenation unit, may aid in further converting MA and PD to ethylene and/or ethane to reduce the concentration of these constituents in the hydrogenated effluent.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the process 10 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the process 10 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for operating an integrated system for producing olefins, the method comprising:
    contacting a hydrogenation feed with a first hydrogenation catalyst to produce a hydrogenated effluent, the hydrogenation feed comprising at least a portion of a first process effluent from a first olefin production process and at least a portion of a second process effluent from a second olefin production process, wherein:
        the hydrogenation feed comprises at least hydrogen, ethylene, carbon monoxide, acetylene, methyl acetylene, and propadiene;
        the first hydrogenation catalyst has a temperature operating range of at least 40 degrees Celsius, the temperature operating range being a difference between a runaway temperature and a cleanup temperature at a given hydrogenation feed composition, wherein the runaway temperature is the temperature at which 3% of ethylene in the hydrogenation feed is reacted and the cleanup temperature is the temperature at which the acetylene concentration in the hydrogenated effluent is equal to a threshold acetylene concentration; and
        the hydrogenated effluent comprises methyl acetylene (MA), propadiene (PD), or both; and
    contacting at least a portion of the hydrogenated effluent with a second hydrogenation catalyst, wherein the contacting causes hydrogenation of at least a portion of the methyl acetylene, propadiene, or both, from the hydrogenated effluent to produce an MAPD hydrogenated effluent having a reduced concentration of methyl acetylene, propadiene, or both compared to the portion of the hydrogenated effluent prior to contact with the second hydrogenation catalyst.

2. The method of claim 1, wherein the first process effluent comprises a cracked gas produced by cracking at least a portion of a first hydrocarbon feed in a steam cracking system, the cracked gas comprising at least hydrogen, carbon monoxide, acetylene, methyl acetylene, and propadiene.

3. The method of claim 1, wherein the second process effluent comprises a fluidized catalytic dehydrogenation (FCDh) effluent produced by dehydrogenating at least a portion of a second hydrocarbon feed in an FCDh system, the FCDh effluent comprising at least hydrogen and carbon monoxide.

4. The method of claim 1, in which a combined concentration of methyl acetylene and propadiene in the portion of the hydrogenated effluent contacted with the second hydrogenation catalyst is less than or equal to 10 wt. %.

5. The method of claim 1, further comprising passing at least a portion of the MAPD hydrogenated effluent to the FCDh system.

6. The method of claim 1, in which the MAPD hydrogenated effluent comprises propane.

7. The method of claim 1, further comprising combining at least a portion of the second hydrocarbon feed with the portion of the hydrogenated effluent before or during contacting of the portion of the hydrogenated effluent with the second hydrogenation catalyst.

8. The method of claim 1, wherein the hydrogenation feed comprises at least 95% of the carbon monoxide from the first process effluent and the second process effluent.

9. The method of claim 1, wherein contact of the hydrogenation feed with the first hydrogenation catalyst produces a conversion of methyl acetylene in the hydrogenation feed of less than 80%.

10. The method of claim 1, wherein contact of the hydrogenation feed with the first hydrogenation catalyst produces a conversion of propadiene in the hydrogenation feed of less than 10%.

11. The method of claim 1, wherein the hydrogenation feed is contacted with the first hydrogenation catalyst in an acetylene hydrogenation unit.

12. The method of claim 11, wherein the first hydrogenation catalyst having a temperature operating range of greater than or equal to 40° C. reduces or prevents thermal runaway of the acetylene hydrogenation unit in response to a disruption in flow of the first process effluent or the second process effluent.

13. The method of claim 1, further comprising separating the first process effluent and the second process effluent into the hydrogenation feed and an acetylene-depleted stream.

14. The method of claim 13, in which a first separation system for separating the first process effluent and the second process effluent into the hydrogenation feed and acetylene-depleted stream has a front end depropanizer configuration.

15. The method of claim 1, in which the threshold acetylene concentration is 1 part per million by volume.

* * * * *